(12) United States Patent
Underwood et al.

(10) Patent No.: US 9,535,578 B2
(45) Date of Patent: Jan. 3, 2017

(54) AUTOMATIC CONFIGURATION OF DISPLAYS FOR SLIDE PRESENTATION

(71) Applicant: Apple Inc., Cupertino, CA (US)

(72) Inventors: David A. Underwood, Arlington, VA (US); Evan S. Torchin, San Francisco, CA (US); Allen W. Lucas, Redwood City, CA (US)

(73) Assignee: Apple Inc., Cupertino, CA (US)

( * ) Notice: Subject to any disclaimer, the term of this patent is extended or adjusted under 35 U.S.C. 154(b) by 370 days.

(21) Appl. No.: 14/058,016

(22) Filed: Oct. 18, 2013

(65) Prior Publication Data

US 2015/0113411 A1   Apr. 23, 2015

(51) Int. Cl.

| | | |
|---|---|---|
| *G06F 3/0484* | (2013.01) | |
| *G06F 3/14* | (2006.01) | |
| *A61B 8/00* | (2006.01) | |
| *G06F 1/16* | (2006.01) | |
| *A61B 5/00* | (2006.01) | |
| *H04N 21/41* | (2011.01) | |
| *G06F 21/84* | (2013.01) | |

(52) U.S. Cl.
CPC ........... *G06F 3/0484* (2013.01); *G06F 3/1423* (2013.01); *A61B 5/7445* (2013.01); *A61B 8/464* (2013.01); *G06F 1/1647* (2013.01); *G06F 21/84* (2013.01); *H04N 21/4122* (2013.01)

(58) Field of Classification Search
CPC .... G06F 3/1423; G06F 1/1647; G06F 1/1641; G06F 3/1446; G06F 1/1654; G06F 21/84; G09G 5/14; G09G 2300/023; G09G 2300/026; H04M 2250/16; A61B 5/7445; A61B 8/464; A63F 13/26; H04N 21/4122
See application file for complete search history.

(56) References Cited

U.S. PATENT DOCUMENTS

| | | | | |
|---|---|---|---|---|
| 5,767,897 A | * | 6/1998 | Howell | ..................... H04N 7/15 348/14.07 |
| 7,373,605 B2 | * | 5/2008 | Schaper | ................ G06F 3/1431 345/1.1 |
| 7,675,479 B2 | * | 3/2010 | Jung | ..................... G06F 3/1446 345/1.1 |
| 8,223,030 B2 | * | 7/2012 | Halpin | .................. G06F 1/1616 340/635 |

(Continued)

*Primary Examiner* — Shen Shiau
(74) *Attorney, Agent, or Firm* — Fletcher Toder PC

(57) ABSTRACT

Systems, methods, and devices are provided for automatically configuring a display layout for a slide presentation to allow a presenter to seamlessly perform effective, professional slide presentation even in unfamiliar locales. A method for doing so may involve receiving connected display information that describes the electronic displays currently connected to the electronic device. When the connected display information indicates that multiple electronic displays are currently connected, the processor of the electronic device may automatically choose, without explicit user assignment, a main presentation display and one or more presenter displays. The main presentation display may display a slide presentation from among the multiple electronic displays, while the presenter displays may display information other than only the slide presentation to aid the presenter. The main presentation display and the presenter displays may be chosen based at least in part on the connected display information.

27 Claims, 16 Drawing Sheets

(56) References Cited

U.S. PATENT DOCUMENTS

| | | | |
|---|---|---|---|
| 2004/0012538 A1* | 1/2004 | Bhogal | G06F 3/1431 345/1.1 |
| 2004/0227692 A1* | 11/2004 | Yoon | G06F 3/1438 345/3.1 |
| 2006/0013462 A1* | 1/2006 | Sadikali | G06F 19/3406 382/132 |
| 2006/0070001 A1* | 3/2006 | Liu | G06F 3/1423 715/732 |
| 2007/0157320 A1* | 7/2007 | Collins | G06F 21/10 726/27 |
| 2008/0165083 A1 | 7/2008 | Brodersen et al. | |
| 2008/0231546 A1* | 9/2008 | Li | G06F 3/1423 345/3.4 |
| 2009/0153435 A1* | 6/2009 | Butler | G06Q 10/10 345/1.3 |
| 2009/0160731 A1 | 6/2009 | Schuler et al. | |
| 2009/0243959 A1* | 10/2009 | Pering | G06F 3/1423 345/1.3 |
| 2010/0261466 A1* | 10/2010 | Chang | G06F 3/1423 455/420 |
| 2010/0321395 A1* | 12/2010 | Maciesowicz | G06F 3/14 345/502 |
| 2011/0202957 A1* | 8/2011 | Cho | G08C 17/02 725/38 |
| 2011/0307788 A1 | 12/2011 | Cheung et al. | |
| 2012/0050183 A1* | 3/2012 | Lee | G06F 3/1423 345/173 |
| 2012/0092235 A1* | 4/2012 | Ham | H04N 21/4122 345/1.3 |
| 2012/0162514 A1 | 6/2012 | Ryu et al. | |
| 2012/0162530 A1* | 6/2012 | Hachiya | H04N 21/4122 348/705 |
| 2012/0236023 A1* | 9/2012 | Yokoyama | H04N 9/3179 345/619 |
| 2012/0297090 A1* | 11/2012 | Manges | G06F 3/1454 709/248 |
| 2013/0210488 A1* | 8/2013 | Lee | G06F 3/14 455/557 |
| 2013/0271558 A1* | 10/2013 | Grimshaw | H04M 3/567 348/14.07 |
| 2013/0321340 A1* | 12/2013 | Seo | G06F 1/1641 345/174 |
| 2014/0137164 A1* | 5/2014 | Yang | H04N 21/2146 725/76 |

* cited by examiner

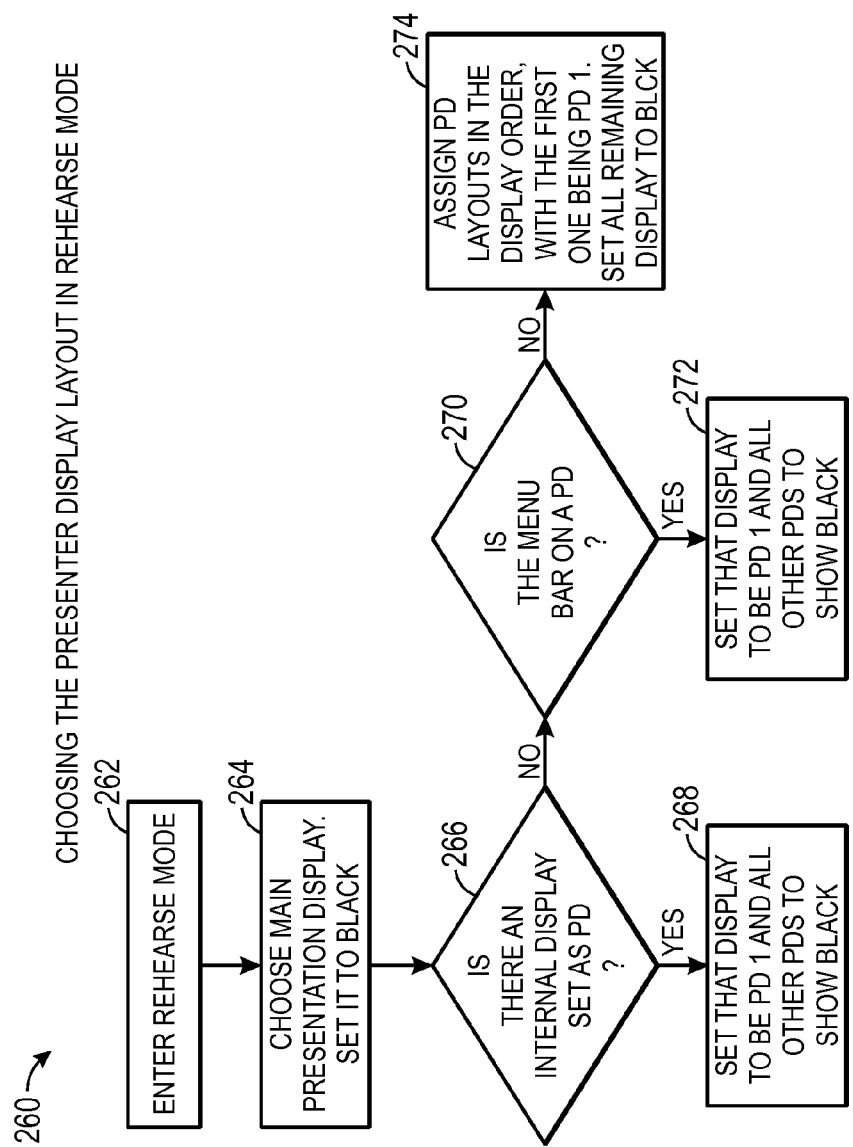

AUTOMATIC CONFIGURATION OF DISPLAYS FOR SLIDE PRESENTATION

BACKGROUND

This disclosure relates to automatically configuring display layouts for slide presentations.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A variety of electronic devices, such as desktop and notebook computers, tablet computers, and similar handheld devices, use electronic displays to display graphical user interfaces (GUIs) and other image data. In some cases, these electronic devices may connect to more than one electronic display. For instance, a user may employ a multi-monitor configuration in which a desktop extends across more than one electronic display connected to an electronic device. In another example, a user may bring a notebook computer into a meeting room and connect to an electronic projector to perform a slide presentation.

When an electronic device employs a multi-display configuration with certain slide presentation programs (e.g., Keynote® by Apple Inc.), a slide presentation may be displayed on one display (e.g., a projector) while other information to aid a presenter is displayed on another display (e.g., a notebook computer screen). Although the presenter may produce beautiful, professional, and effective slide presentations using such a presentation program, operating in a multi-display configuration may entail some user configuration of the displays. When a presenter connects to multiple displays to give a presentation, however, the presenter may want the audience only to see the presentation, and not any other materials that might be used to aid the presenter. Connecting to multiple electronic displays and then selecting and/or configuring the multiple displays may be frustrating to the presenter and may reveal the assistive information to the audience.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

This disclosure relates to systems, methods, and computer program products for automatically configuring electronic displays for a slide presentation. Indeed, when a presenter connects an electronic device to an unfamiliar set of electronic displays, or when a presenter connects the electronic device to a set of electronic displays the presenter has previously configured, the electronic device may automatically configure the electronic displays based on at least some of the characteristics of the electronic displays. In one example, the electronic device may identify that the presenter has previously configured a display layout for the set of electronic displays now connected. In response, the electronic device may automatically apply the previous display layout. In another example, the electronic device may automatically select a display layout that is most likely to be appropriate given the characteristics of the electronic displays. A projector or a television, for example, may more likely be appropriate to be a main presentation display that displays the slide presentation than an internal display. Under these circumstances, the electronic device may choose the projector or television to be the main presentation display and choose the internal display to be a presenter display that provides other information to aid the presenter. In this way, a presenter may seamlessly and professionally perform presentations—even in unfamiliar locations or with late notice—without first configuring the display configuration while the audience watches and waits.

BRIEF DESCRIPTION OF THE DRAWINGS

Various aspects of this disclosure may be better understood upon reading the following detailed description and upon reference to the drawings in which:

FIG. 16 is a flowchart for determining a presenter display (PD) layout in a rehearse mode of a presentation program, in accordance with an embodiment.

DETAILED DESCRIPTION

Figure 1:
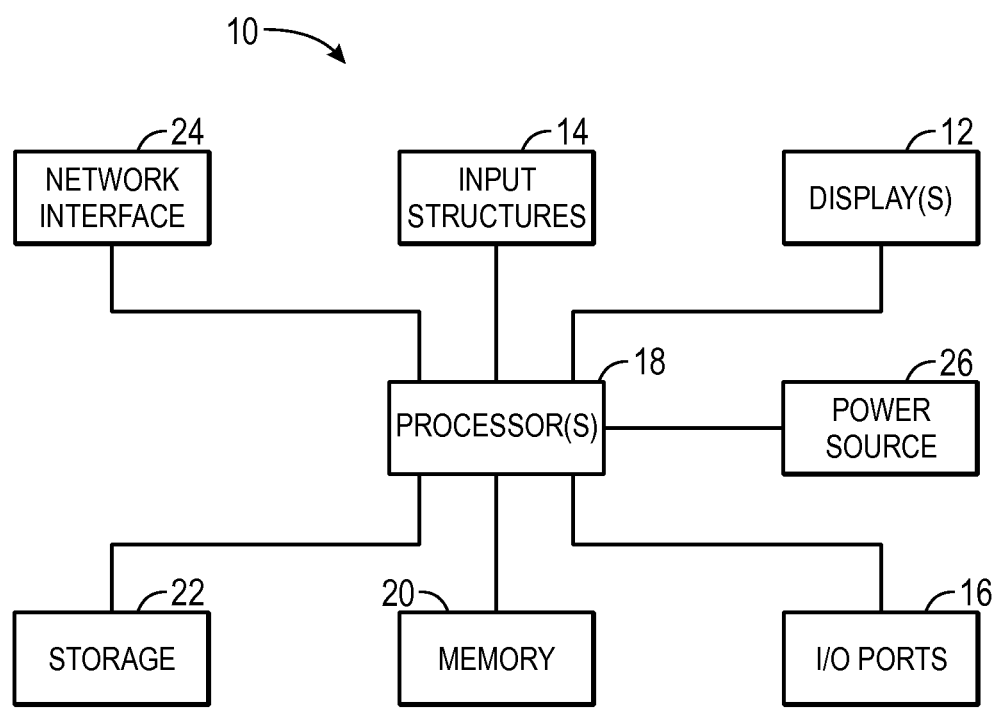
FIG. 1 is a block diagram of an electronic device that may use the techniques disclosed herein, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A slide presentation program, such as the Keynote® presentation application program by Apple Inc. of Cupertino, Calif., may allow a user to create professional, effective, and visually stunning slide presentations. On an electronic device that is connected to only one display, that single electronic display may operate as a main presentation (MP) display on which the presentation audience can view the slide presentation. When more than one electronic display is connected to the electronic device, one of the connected displays may be the main presentation (MP) display, while other connected displays may operate as presenter displays (PDs) that provide various information to assist the presenter, such as the representations of the current and/or next slide, a current time of day, a timer of remaining or elapsed time, and/or presentation notes.

This disclosure provides systems, methods, and devices for seamless and professional operation in a multi-display environment. Using the disclosed techniques, a presenter may perform a presentation on a multi-display layout without individually configuring the displays each time the electronic displays that are connected to the electronic device change. Indeed, presenters frequently perform slide presentations in locations with sets of electronic displays other than those used natively by the presenter and/or the presenter's electronic device. In many cases, a presenter brings his or her personal notebook computer into a meeting room. There, the presenter connects the notebook computer to an external display, such as a projector or television, that serves as the main point of focus in the room. According to the techniques of this disclosure, the presenter may not need to specifically configure the set of connected displays. Rather, the presenter's electronic device may automatically configure a presentation display layout—selecting, for example, a main presentation (MP) display and one or more presenter displays (PDs)—for the set of connected electronic displays based at least in part on connected display information describing the displays.

In one example, when a presenter connects or disconnects an electronic display to an electronic device running a slide presentation program, the electronic device may automatically determine which connected display is appropriate to be a main presentation (MP) display (e.g., a projector or television) and which electronic display(s) should be presenter displays (PDs) (e.g., an internal display). In fact, the electronic device may even determine which of the presenter displays (PDs) should be a primary presenter display (PD1) that includes various user interface (UI) control features, and which should be secondary presenter displays (PD2, PD3, PD4, and so forth) that display information relating to the presentation but which may not include the control features. The audience may never see the presenter displays (PDs) and the presentation may proceed in a seamless, professional manner.

Figure 2:
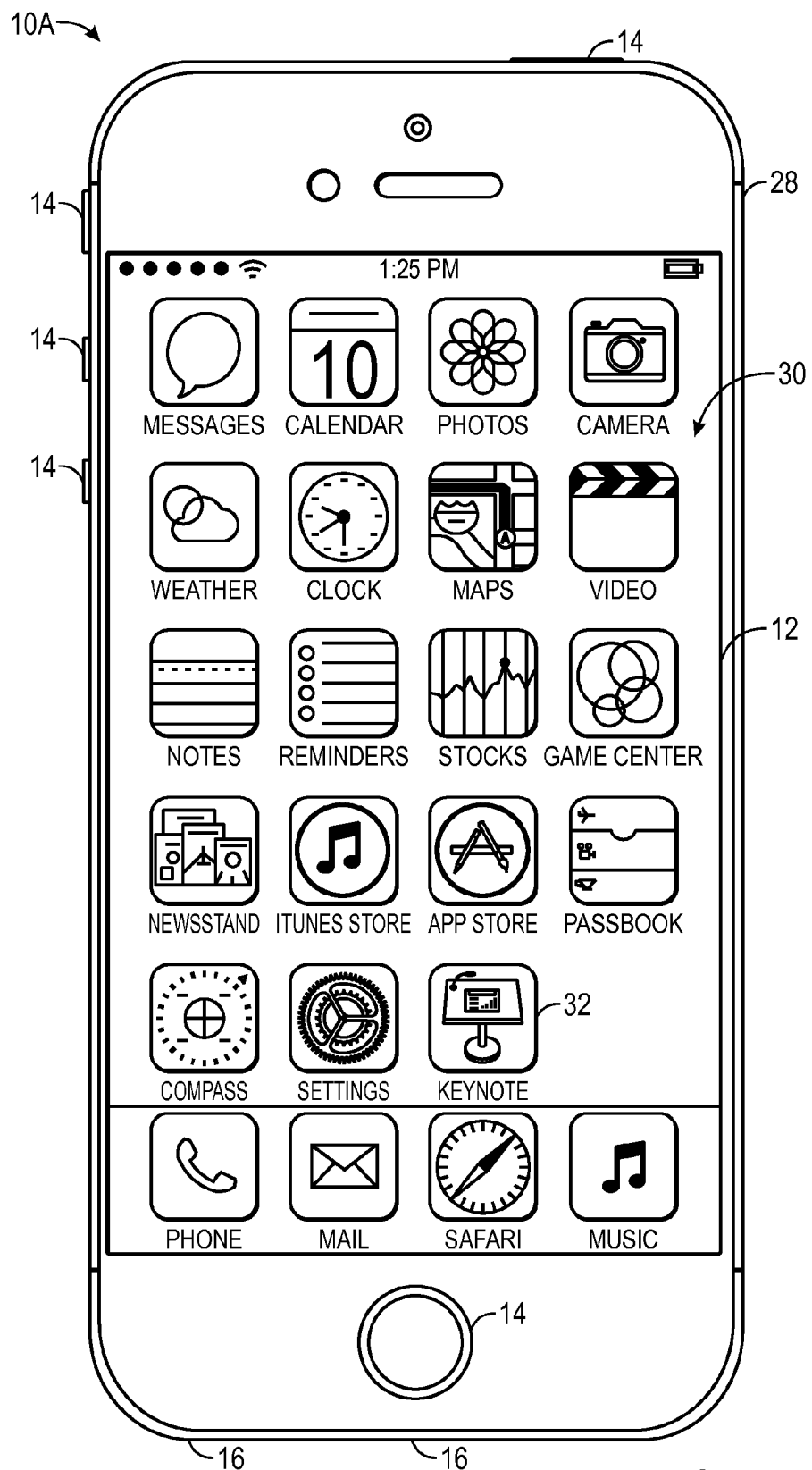
FIG. 2 is a front view of a handheld device, such as an iPhone® by Apple Inc., representing an example of the electronic device of FIG. 1.
Figure 3:
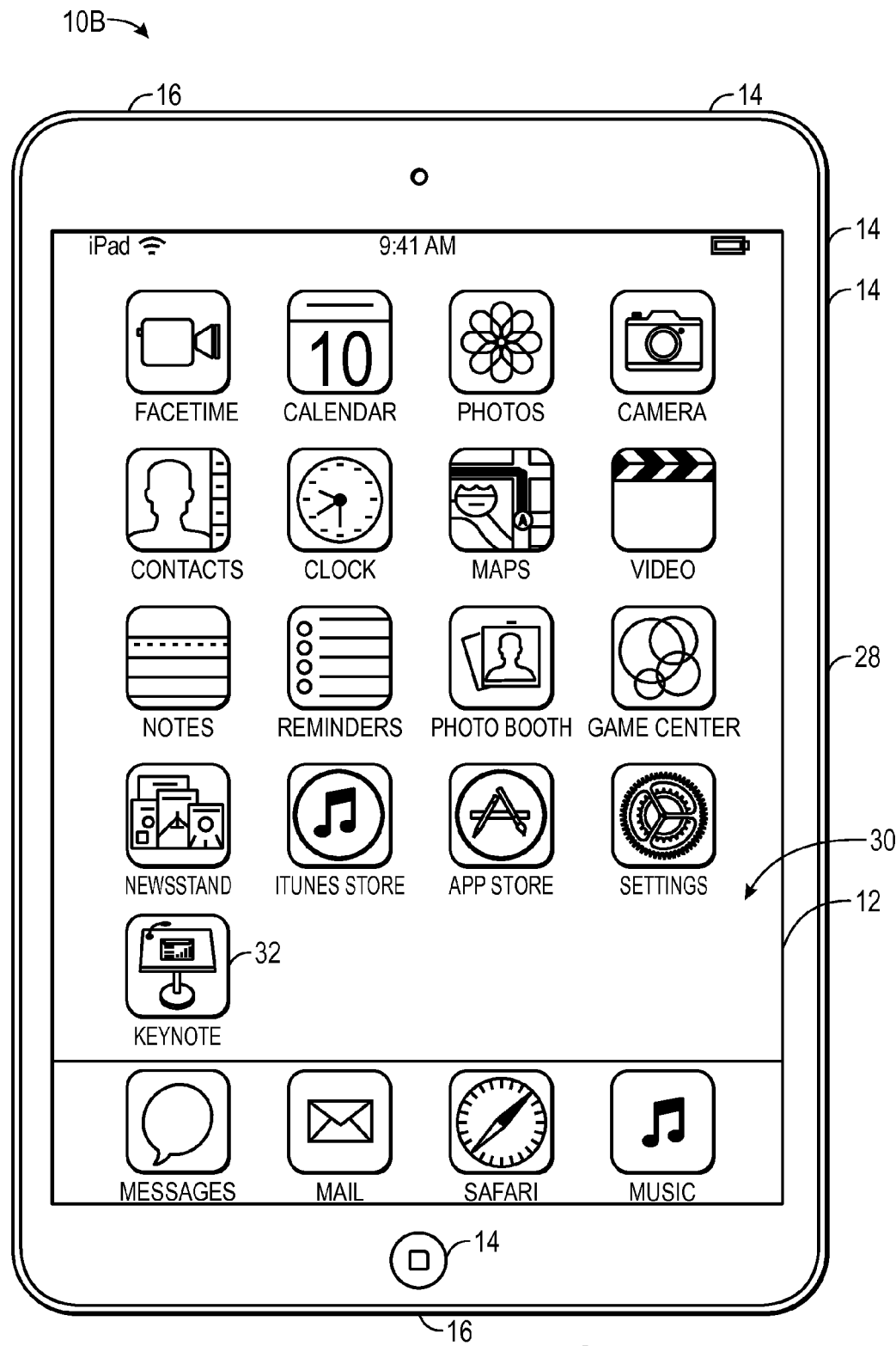
FIG. 3 is a front view of a tablet device, such as an iPad® by Apple Inc., representing an example of the electronic device of FIG. 1.
Figure 4:
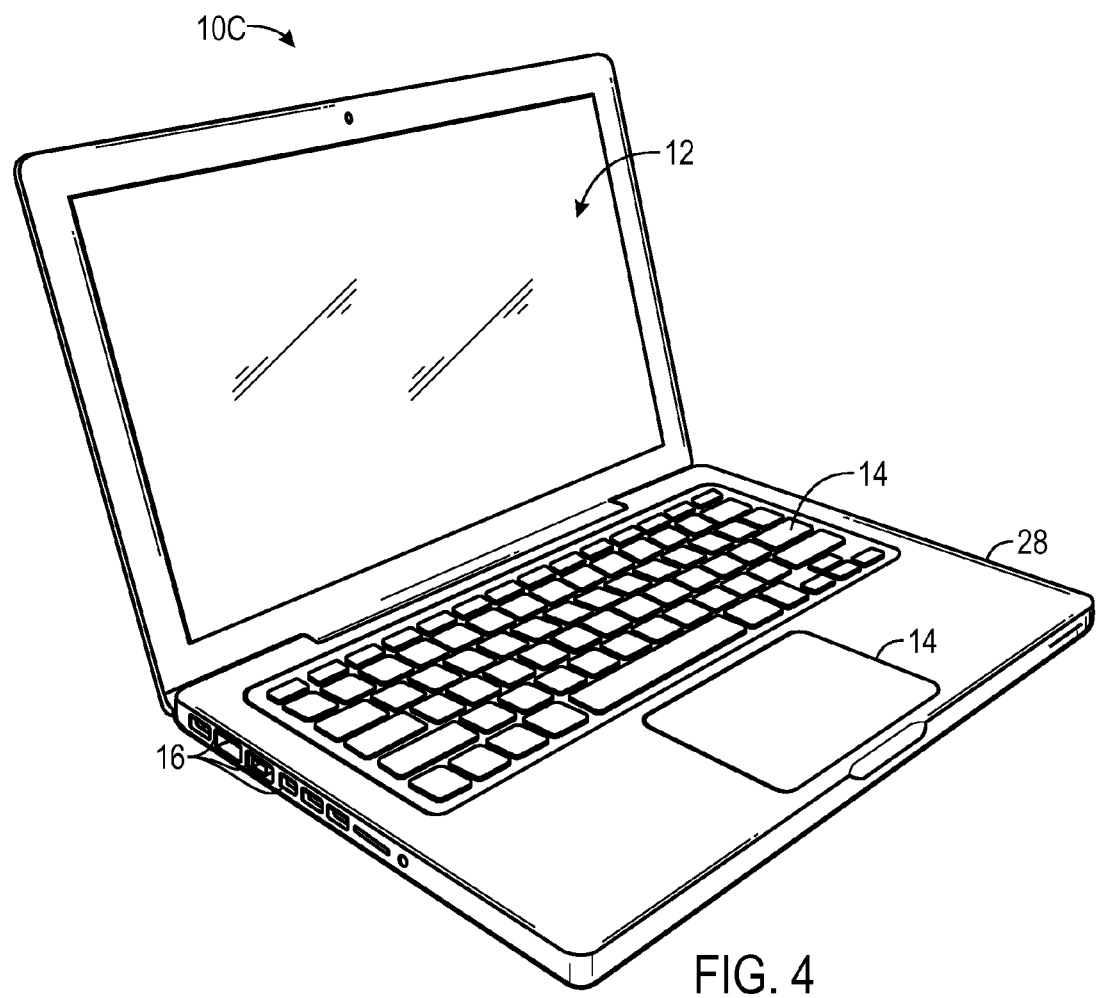
FIG. 4 is a perspective view of a notebook computer, such as a MacBook Pro® by Apple Inc., representing an example of the electronic device of FIG. 1.

A variety of suitable electronic devices may employ the techniques described below. FIG. 1, for example, is a block diagram depicting various components that may be present in a suitable electronic device 10. FIGS. 2, 3, and 4 illustrate example embodiments of the electronic device 10, depicting a handheld electronic device, a tablet computing device, and a notebook computer, respectively.

Turning first to FIG. 1, the electronic device 10 may include, among other things, a display 12, input structures 14, input/output (I/O) ports 16, one or more processor(s) 18, memory 20, nonvolatile storage 22, a network interface 24, and a power source 26. The various functional blocks shown in FIG. 1 may include hardware elements (including circuitry), software elements (including computer code stored on a non-transitory computer-readable medium) or a combination of both hardware and software elements. It should be noted that FIG. 1 is merely one example of a particular implementation and is intended to illustrate the types of components that may be present in the electronic device 10. Indeed, the various depicted components (e.g., the processor(s) 18) may be separate components, components of a single contained module (e.g., a system-on-a-chip device), or may be incorporated wholly or partially within any of the other elements within the electronic device 10. The components depicted in FIG. 1 may be embodied wholly or in part as machine-readable instructions (e.g., software or firmware), hardware, or any combination thereof.

By way of example, the electronic device 10 may represent a block diagram of the handheld device depicted in FIG. 2, the tablet computing device depicted in FIG. 3, the notebook computer depicted in FIG. 4, or similar devices, such as desktop computers, televisions, and so forth. In the electronic device 10 of FIG. 1, the display 12 may be any suitable electronic display used to display image data (e.g., a liquid crystal display (LCD) or an organic light emitting diode (OLED) display). Moreover, the electronic device 10 may connect to one or more external electronic displays 12 in various embodiments. Doing so may allow a variety of different information to be displayed on each of the multiple electronic displays 12. In some examples, the display 12 may represent one of the input structures 14, enabling users to interact with a user interface of the electronic device 10. In some embodiments, the electronic display 12 may be a MultiTouch™ display that can detect multiple touches at once. Other input structures 14 of the electronic device 10 may include buttons, keyboards, mice, trackpads, and the like. The I/O ports 16 may enable electronic device 10 to interface with various other electronic devices.

The processor(s) 18 and/or other data processing circuitry may execute instructions and/or operate on data stored in the memory 20 and/or nonvolatile storage 22. The memory 20 and the nonvolatile storage 22 may be any suitable articles of manufacture that include tangible, non-transitory computer-readable media to store the instructions or data, such as random-access memory, read-only memory, rewritable flash memory, hard drives, and optical discs. By way of example, a computer program product containing the instructions may include an operating system (e.g., OS X® or iOS by Apple Inc.) or an application program (e.g., Keynote® by Apple Inc.).

The network interface 24 may include, for example, one or more interfaces for a personal area network (PAN), such as a Bluetooth network, for a local area network (LAN), such as an 802.11x Wi-Fi network, and/or for a wide area network (WAN), such as a 4G or LTE cellular network. The power source 26 of the electronic device 10 may be any suitable source of energy, such as a rechargeable lithium polymer (Li-poly) battery and/or an alternating current (AC) power converter.

As mentioned above, the electronic device 10 may take the form of a computer or other type of electronic device. Such computers may include computers that are generally portable (such as laptop, notebook, and tablet computers) as well as computers that are generally used in one place (such as conventional desktop computers, workstations and/or servers). FIG. 2 depicts a front view of a handheld device 10A, which represents one embodiment of the electronic device 10. The handheld device 10A may represent, for example, a portable phone, a media player, a personal data organizer, a handheld game platform, or any combination of such devices. By way of example, the handheld device 10A may be a model of an iPod® or iPhone® available from Apple Inc. of Cupertino, Calif.

The handheld device 10A may include an enclosure 28 to protect interior components from physical damage and to shield them from electromagnetic interference. The enclosure 28 may surround the display 12, which may display a graphical user interface (GUI) 30 having an array of icons 32. By way of example, one of the icons 32 may launch a presentation application program (e.g., Keynote® by Apple Inc.). User input structures 14, in combination with the display 12, may allow a user to control the handheld device 10A. For example, the input structures 14 may activate or deactivate the handheld device 10A, navigate a user interface to a home screen, navigate a user interface to a user-configurable application screen, activate a voice-recognition feature, provide volume control, and toggle between vibrate and ring modes. Touchscreen features of the display 12 of the handheld device 10A may provide a simplified approach to controlling the presentation application program. The handheld device 10A may include I/O ports 16 that open through the enclosure 28. These I/O ports 16 may include, for example, an audio jack and/or a Lightning® port from Apple Inc. to connect to external devices. The electronic device 10 may also be a tablet device 10B, as illustrated in FIG. 3. For example, the tablet device 10B may be a model of an iPad® available from Apple Inc.

In certain embodiments, the electronic device 10 may take the form of a computer, such as a model of a MacBook®, MacBook® Pro, MacBook Air®, iMac®, Mac® mini, or Mac Pro® available from Apple Inc. In this disclosure, an integrated internal electronic display 12 is understood to be connected to the electronic device, even though it may be integral to the electronic device 10. Thus, when many of the following examples describe a computer in the form of a notebook computer 10C, as illustrated in FIG. 4, it should be understood that the integrated internal electronic display 12 is considered to be connected to the computer 10C for purposes of automatically assigning roles to the various displays 12 that the computer 10C is connected to. The depicted computer 10C may include the integrated internal display 12, input structures 14, I/O ports 16, and a housing 28. In one embodiment, the input structures 14 (e.g., a keyboard and/or touchpad) may be used to interact with the computer 10C, such as to start, control, or operate a GUI or applications (e.g., Keynote® by Apple Inc.) running on the computer 10C.

Figure 5:
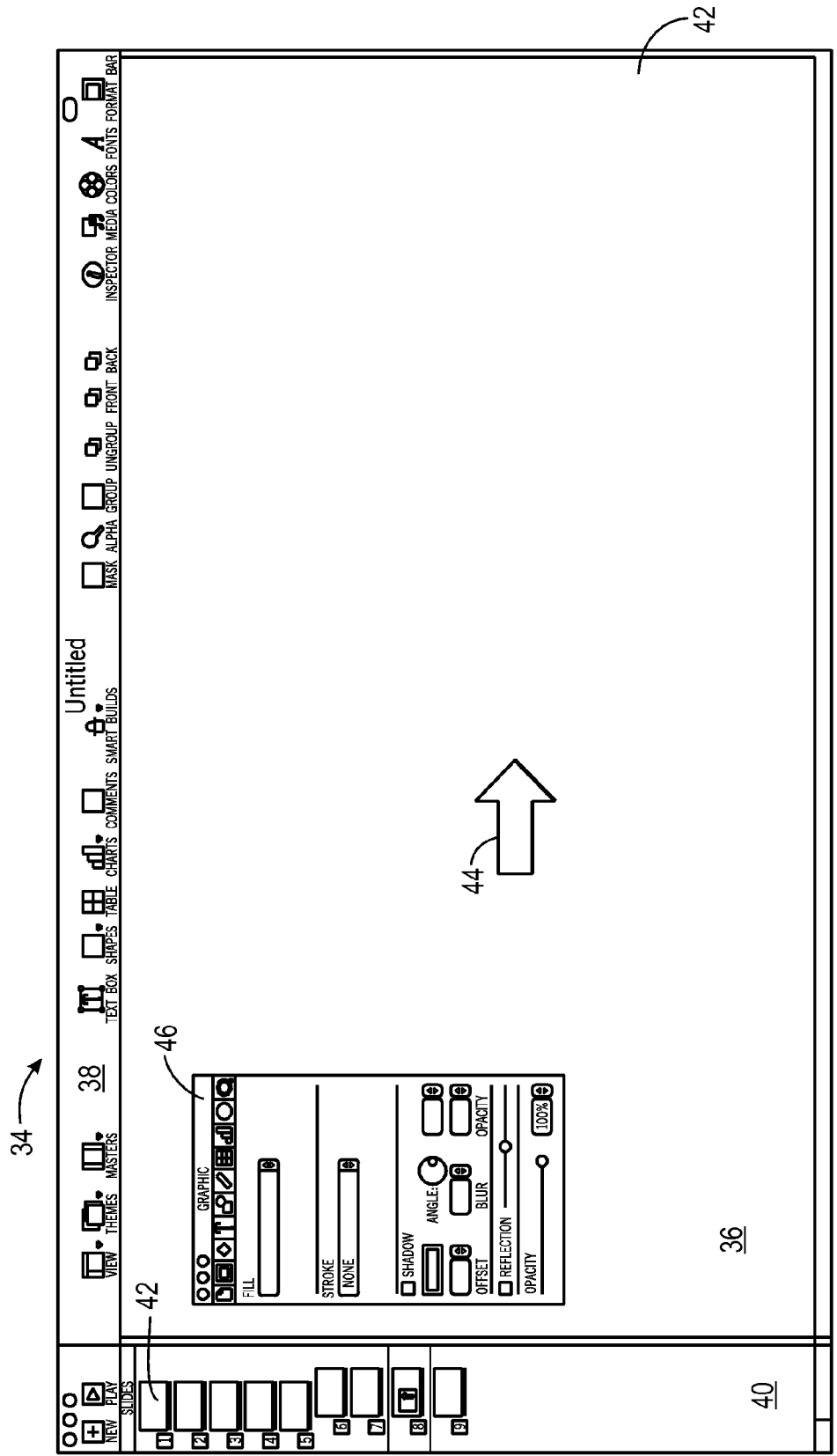
FIG. 5 illustrates a edit mode screen of a presentation program in accordance with aspects of the present disclosure.

With the foregoing in mind, a variety of computer program products, such as applications or operating systems, may use the techniques discussed below to enhance the user experience on the electronic device 10. For instance, the electronic device 10 may run a presentation program 34 (e.g., Keynote® from Apple Inc.) as shown in FIG. 5. The presentation program 34 shown in FIG. 5 may provide multiple modes of operation, such as an edit mode and a presentation mode. In FIG. 5, the presentation program 34 is shown in the edit mode. In the edit mode, the presentation program may provide a convenient and user-friendly interface for a user to add, edit, remove, or otherwise modify the slides of a slide show. To this end, the presentation program 34 may include three panes: a canvas 36, a toolbar 38, and a slide organizer 40. The canvas 36 may display a currently selected slide 42 from among the slide organizer 40. A user may add content to the canvas 36 using tool selections from the toolbar 38. Among other things, this content may include objects 44 such as text boxes, images, shapes, and/or video objects. When in the edit mode, the user may add or remove objects and/or may assign actions and/or effects to one or more of the objects. In the presentation mode, the user may display a created slide or a sequence of slides in a format suitable for audience viewing. In some embodiments, the presentation program may provide a full-screen presentation of the slides in the presentation mode, including any animations, transitions, or other properties defined for each object within the slides.

As used herein, the term "object" refers to any individually editable component on a canvas (e.g., the canvas 36 of the presentation program 34). That is, content that can be added to a slide and/or be altered or edited on the slide may constitute an object. For example, a graphic, such as an image, photo, line drawing, clip art, chart, or table, that may be provided on a slide may constitute an object. In addition, a character or string of characters may constitute an object. Likewise, an embedded video clip may also constitute an object that is a component of a slide. Applying changes or alterations of an object, such as to change its location, size, orientation, appearance or to change its content, may be understood to be changing a property of the object. Therefore, in certain embodiments, characters and/or character strings (alphabetic, numeric, and/or symbolic), image files (.jpg, .bmp, .gif, .tif, .png, .cgm, .svg, .pdf, .wmf, and so forth), video files (.avi, .mov, .mp4, .mpg, .qt, .rm, .swf, .wmv, and so forth) and other multimedia files or other files in general may constitute "objects" as used herein. In certain graphics processing contexts, the term "object" may be used interchangeably with terms such as "bitmap" or "texture."

As used herein, a "slide" should be understood to refer to such a discrete unit of an ordered or sequential presentation. Such a slide, therefore, may be understood to function as a container for a set of objects (as discussed below) that together convey information about a concept. For example, a slide may contain or include different types of multimedia objects (e.g., text, numbers, images, videos, charts, graphs, and/or audio, and so forth) that explain or describe a concept to which the slide is directed and which may be handled or manipulated as a unit due to their being associated with or contained on the slide unit.

Further, because a slide may contain multiple objects, a slide may have an associated z-ordering of those objects as they are displayed on the slide. That is, to the extent that objects on the slide may overlap or interact with one another, they may be ordered or layered with respect to a viewer such that some objects are on top of or beneath other objects as they appear on the slide. In this way, a slide may not only have a width and length associated with it, but also a depth. The order or sequence of the slides in a presentation or slideshow is typically relevant in that the information on the slides (which may include both alphanumeric (text and numbers) and graphical components) is meant to be presented in order or sequence and may build upon itself, such that the information on later slides is understandable in the context of information provided on preceding slides. That is, there is a narrative or explanatory flow associated with the ordering or sequence of the slides. As a result, if presented out of order, the information on the slides may be unintelligible or may otherwise fail to properly convey the information contained in the presentation. This should be understood to be in contrast to more simplistic or earlier usages of the term "slide" and "slideshow" where what was typically shown was not a series of multimedia slides containing sequentially ordered content, but projected photos or images which could typically be displayed in any order without loss of information or content.

As mentioned above, the depicted example screen shown in FIG. 5 includes three panes: a slide canvas 36, a toolbar 38, and a slide organizer 40 for creating and editing various aspects of a slide of a presentation. With these panes, a user may select a slide of a presentation, add and/or edit the contents of a slide, and animate or add effects related to the contents of a slide. It should be understood that the size of each pane is merely illustrative, and that the relative size of each pane may vary or be adjusted by a user.

The slide organizer 40 may display a representation of each slide of a presentation that is being generated or edited. The slide representations may take on a variety of forms, such as an outline of the text in the slide or a thumbnail image of the slide. The slide organizer 40 may allow the user to organize the slides prepared using the application. For example, the user may determine or manipulate the order in which the slides are presented by dragging a slide representation from one relative position to another. As illustrated in FIG. 5, the slide representations in the slide organizer 40 may be indented or otherwise visually set apart for further organizational clarity.

Selecting a slide representation in the slide organizer 40 may result in the presentation program displaying the corresponding slide (e.g., slide 42) on the canvas 36. The selected slide 42 may include one or more suitable objects 44 such as, for example, text, images, graphics, video, or any other suitable object. A user may add or edit features or properties of the selected slide 42 when displayed on the slide canvas 36. For example, a user may edit settings or properties associated with the selected slide 42 (e.g., the slide background or template) on the canvas 36 or may edit the location, orientation, size, properties, and/or animation of objects (e.g., object 44) in the selected slide. The user may select a different slide to be displayed for editing on slide canvas 36 by selecting a different slide representation from the slide organizer 40.

In the depicted implementation, a user may customize objects 44 associated with the slide 42 or the properties of the slide 42 using various tools provided by the presentation program 34 in association with the canvas 36. For example, the toolbar 38 may provide various icons that activate respective tools and/or functions that may be used in creating or editing the slide 42. For example, the toolbar 38 may include an icon that, when selected, activates a build tool that allows one or more objects (e.g., images, tables, videos, etc.) to be selected and/or grouped. Animations (motion, rotation, changes in size, shading, color, opacity, and so forth) may be generated for such selected objects or groups of objects. In some embodiments, the animations may be rendered in real-time (e.g., using dedicated graphics circuitry, such as a GPU on a video card) when slides containing the animations are displayed or presented as part of a presentation.

In some embodiments, the presentation program 34 may allow a control window 46 to be opened or displayed. The presentation program 34 may display the control window 46 automatically (e.g., based on the presentation program context) or in response to a user instruction (e.g., in response to a user instruction to display options related to one or more selected objects). The control window 46 may be moved, resized, and/or minimized/maximized independently of the panes 36, 38, and 40 (e.g., as an overlaid window). The control window 46 may provide one or more user input mechanisms of any suitable type, such as drop down menus, radio buttons, sliders, and so forth. The options available from control window 46 may vary based on a tool selected in toolbar 38 or by a type of object(s) 44 selected on the slide 42. For example, the control window 46 may provide different respective options if a table, video, graphic, or text is selected on the slide 42 or if no object 44 is selected. It should be understood that although only one control window 46 is shown in FIG. 5, the presentation program 34 may include any suitable number of control window 46.

Figure 6:
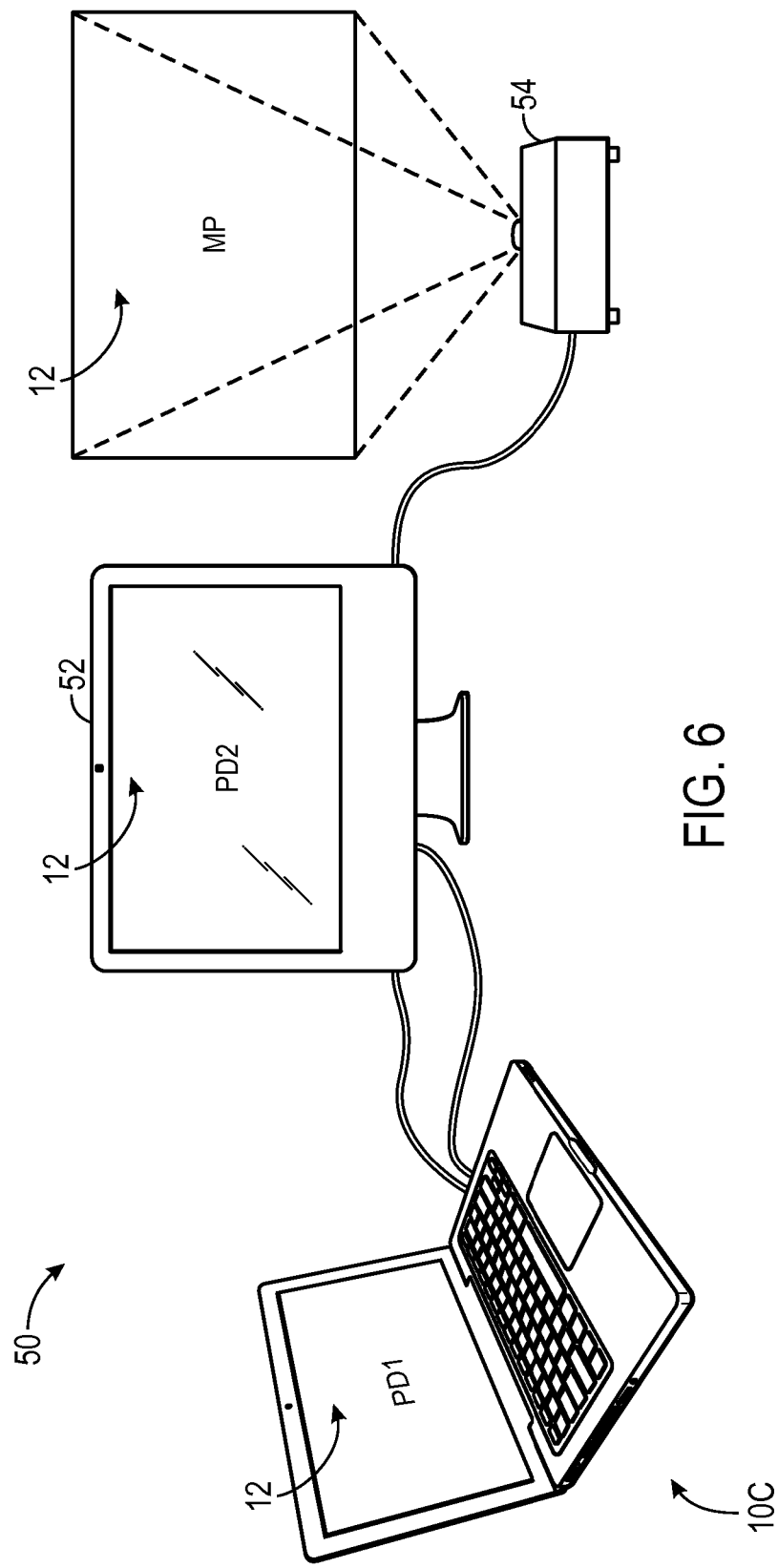
FIG. 6 is a perspective view of a multi-display presentation display layout for a slide presentation, in accordance with an embodiment.

The presentation program may also include a presentation mode, which may also be referred to as a play mode, that can employ a multi-display layout 50 such as that shown in FIG. 6. In the example of FIG. 6, an electronic device 10 (here, a notebook computer 10C) running the presentation program in presentation mode is connected to two other external displays 12 (here, a television 52 and a projector 54). The notebook computer 10C may connect to the external displays 12 using any suitable display connection, including Thunderbolt®, DisplayPort®, High-Definition Multimedia Interface (HDMI), or the like. When an electronic device 10 such as the notebook computer 10C connects to external displays 12 such as the television 52 and the projector 54, the electronic device 10 may automatically configure the multi-display presentation layout 50. For instance, the projected imagery representing an electronic display 12 of the projector 54 may be automatically selected to be the main presentation (MP) display, the internal display 12 of the notebook computer 10C may be automatically selected to be the primary presenter display (PD1), and the electronic display 12 of the television 52 may be automatically selected to be a secondary presenter display (PD2).

As should be appreciated, the main presentation (MP) display displays the slide presentation created by the presenter in the edit mode of the presentation program. The presenter displays (PDs), including the primary presenter display (PD1) and any secondary presentation displays (PD2, PD3, PD4, and so forth) may be used to display any suitable information and/or navigational tools other than a fullscreen view of the slide presentation that may aid the presenter in performing the presentation. Some features that may be found in the presenter displays (PDs) will be described by way of example in FIGS. 7-12, discussed below.

Figure 7:
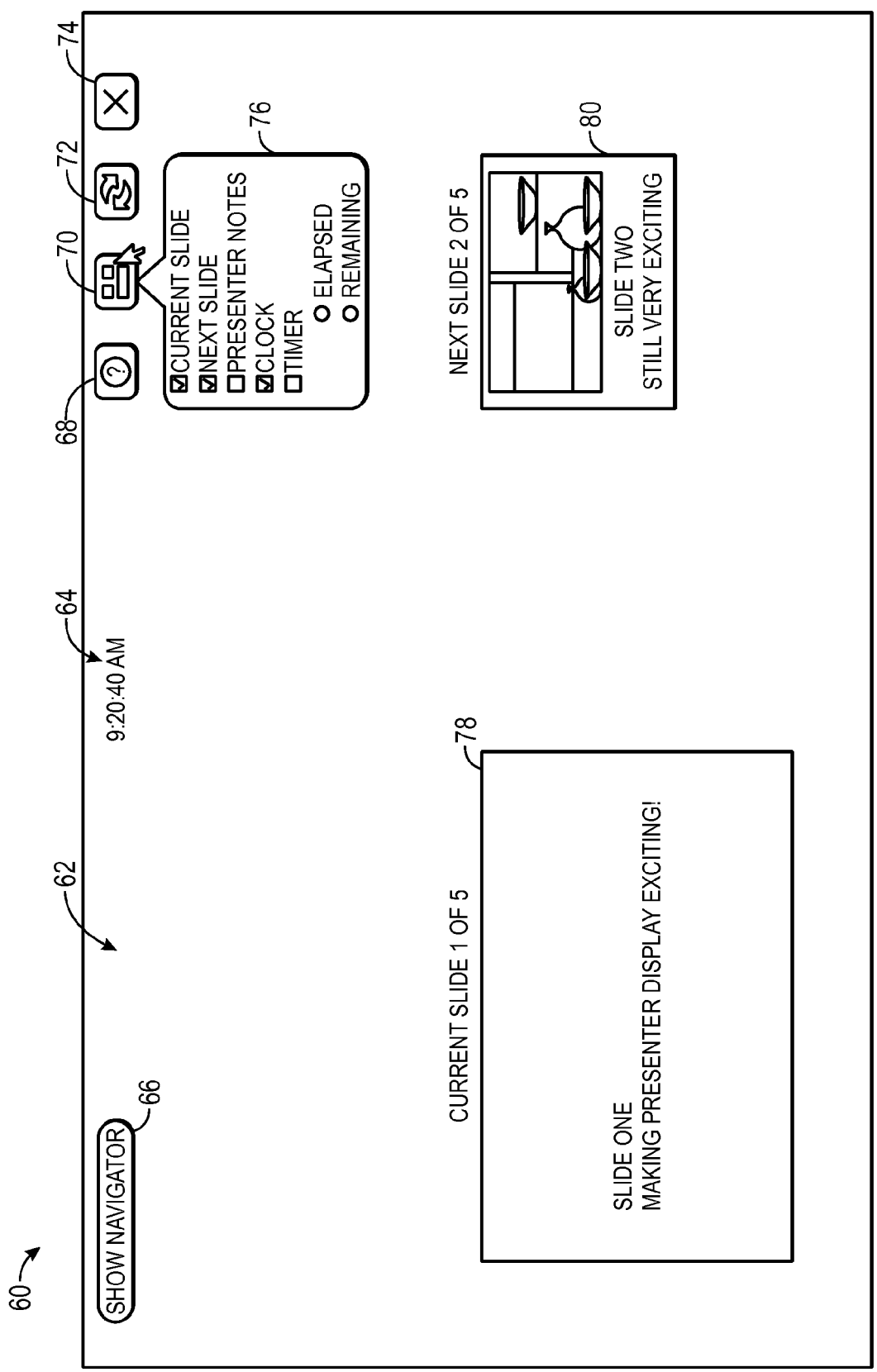
FIGS. 7-11 are examples of screens of presenter displays (PDs) used to provide information to a aid a presenter performing a presentation, in accordance with an embodiment.

In FIG. 7, for example, a screen 60 illustrates an example of a primary presenter display (PD1). As used herein, a primary presenter display (PD1) may include a control interface, such as a control tool bar 62, to enable the presenter to perform certain control features. The control tool bar 62 may, if desired, include a clock 64. A "show navigator" selection button 66 may enable the presenter to navigate from slide to slide in the slide presentation. An example of the navigator provided by the "show navigator" selection button 66 will be discussed further below with reference to FIG. 9.

Still considering the screen 60 of FIG. 7, the control tool bar 62 may also include other user-selectable icons to enable control over features of the slide presentation program. For example, an information icon 68 may enable the presenter to access information relating to the slide presentation, such as document properties, and so forth. A display layout icon 70 may enable the presenter to configure the various displays 12 currently connected to the electronic device 10 as the main presentation (MP) display or as presentation displays (PDs) that display selectable information. A switch display button 72 may cause the primary presenter display (PD1) to become the main presentation (MP) display, and vice versa. An exit mode button 74 may allow the presenter to exit the presentation mode and return to edit mode.

In the example of FIG. 7, the primary presenter display (PD1) represented by the screen 60 is, by way of example, the only presenter display (PD) connected to the electronic device 10 that is running the presentation program. As such, selecting the display layout icon 70 may cause a configuration pane 76 to permit a user to select whether certain information is displayed on the screen 60. Information relating to the current presentation that may aide the presenter may include, for example, a current slide, a next slide, presenter notes, a clock, and/or a timer (e.g., a selectable amount of elapsed or remaining time). As seen in FIG. 7, a current slide, next slide, and clock have been selected to be displayed on the screen 60. Indeed, the top of the screen 60 includes the clock 64, while the central region of the screen 60 includes a representation 78 of a current slide and a representation 80 of the next slide in the slide presentation.

Figure 8:
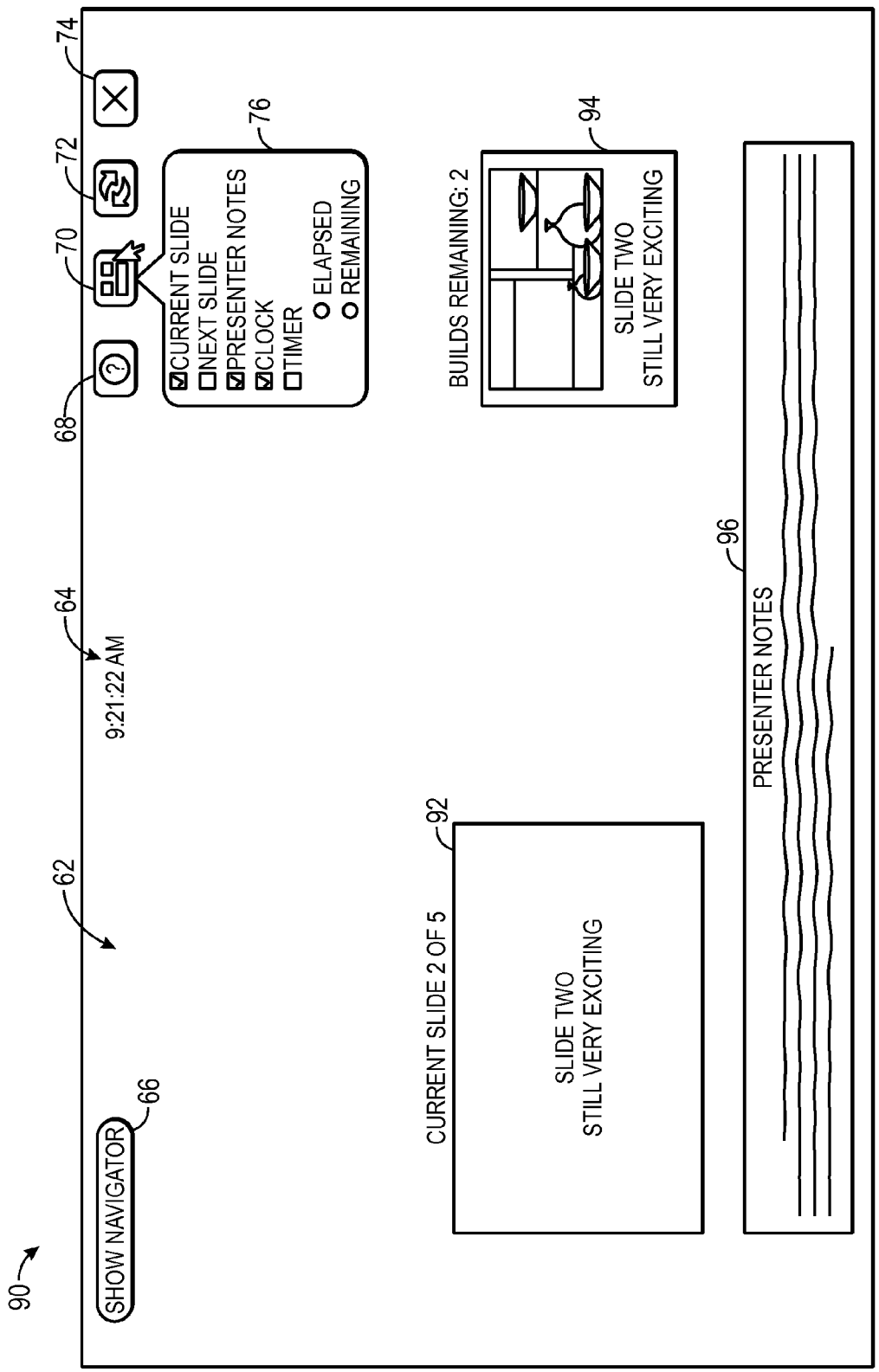
Figure 9:
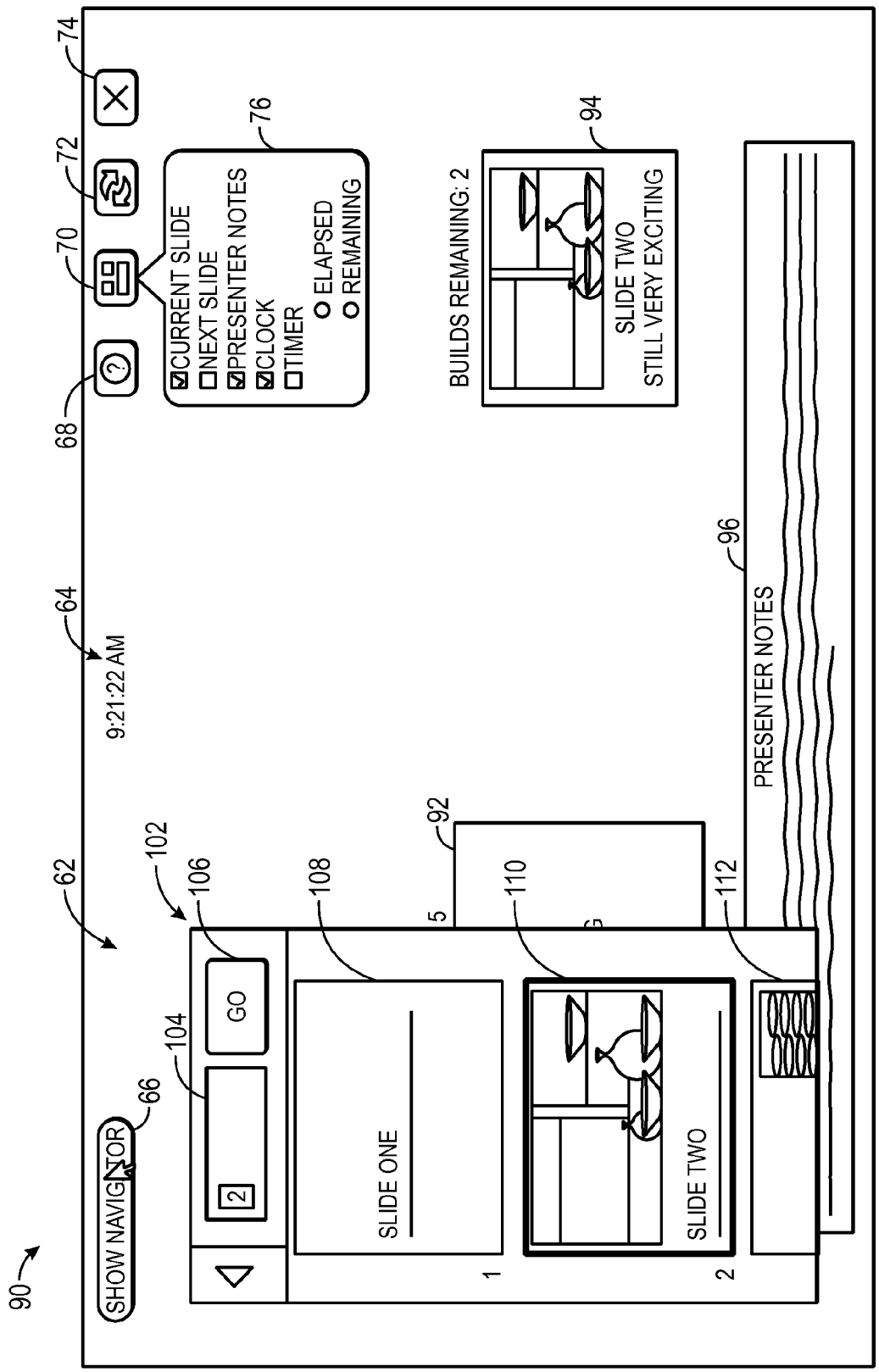

By selecting different information to display from the configuration pane 76, a presenter may view a variety of information that may aid the presenter in carrying out a successful presentation. Selecting an option to display a current slide, presenter notes, and a clock in the configuration pane 76 may yield, for example, an example screen 90 shown in FIG. 8. In the example of FIG. 8, the primary presenter display (PD1) displays the screen 90, which includes a representation 92 of a current view of the current slide and a representation 94 of the completed view once the various animated builds have occurred. Presenter notes 96 are shown at the bottom of the screen 90, although the presenter notes 96 may alternatively be located in other suitable region of the screen 90. Selecting the navigator button 66 may cause a navigator pane 102 to be shown on the primary presenter display (PD 1), as generally shown in an example screen 100 of FIG. 9. The navigator pane 102 may include a slide selection text entry 104 and an inner button 106 (here, labeled "go"), to enable the presenter to jump directly to a desired slide in the slide presentation. Slide representations 108, 110, and 112 provide thumbnail images of the slides of the slide presentation that the presenter may select.

Figure 10:
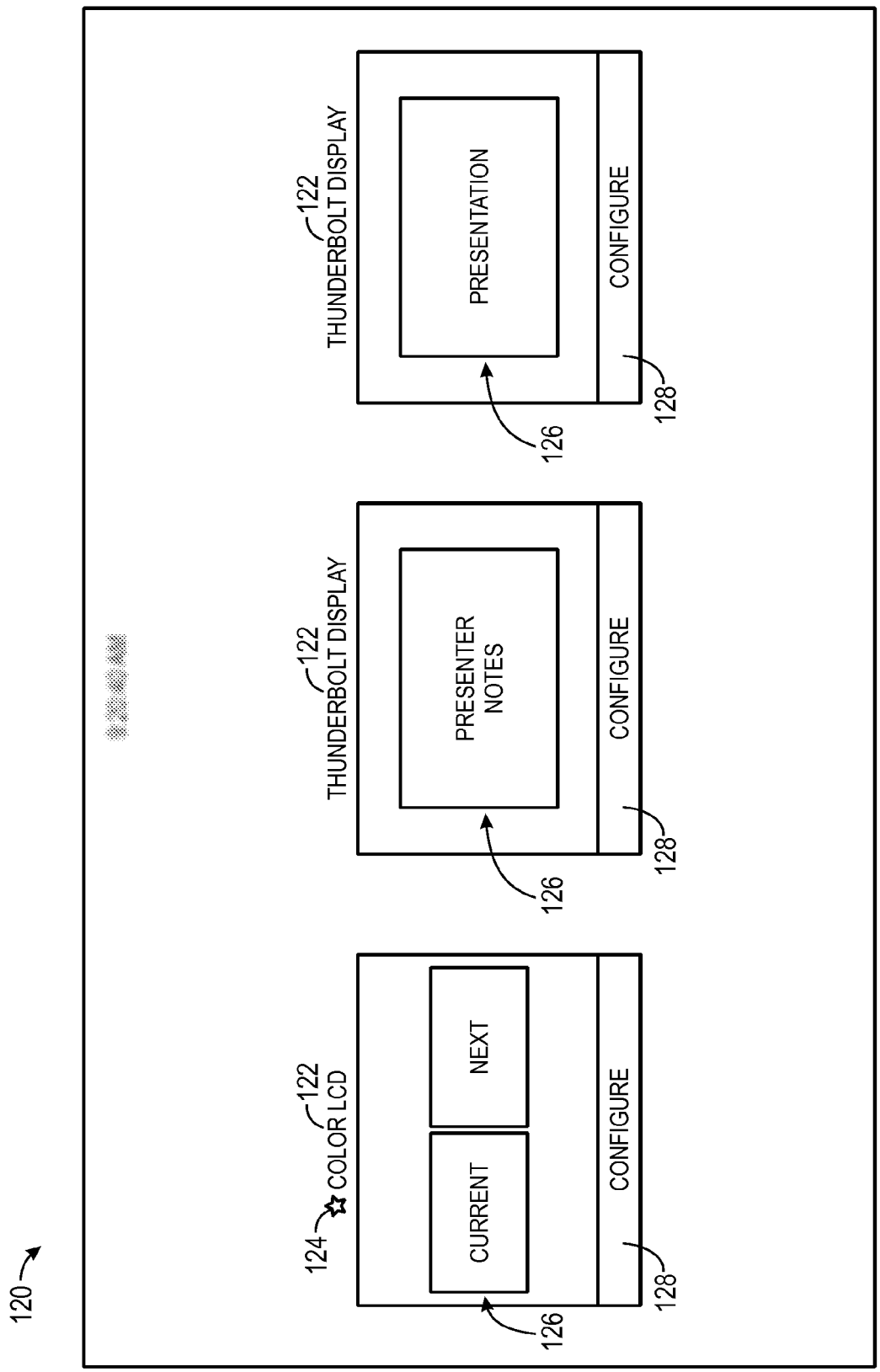

When more than two electronic displays are connected to the electronic device 10 (e.g., as illustrated in FIG. 6, discussed above), selecting the display configuration icon 70 on the primary presenter display (PD1) may enable the presenter to configure each of the electronic displays 12 as presenter displays (PDs) or as the main presentation (MP) display. For instance, a configuration screen 120, shown in FIG. 10, may appear to enable the presenter to configure the various electronic displays 12. In the example of FIG. 10, text 122 indicates the type of displays 12 and/or the name of the displays 12 that are currently connected to the electronic device 10. A primary display indicator 124 may denote which of the configurable displays is the primary presenter display (PD1). Thumbnail representations 126 of the various displays 12 may provide a simple and effective view of all of the layout of the various displays 12. Configuration buttons 128 beneath each of the thumbnail representations 126 may allow the presenter to configure each of the displays 12 individually.

Figure 11:
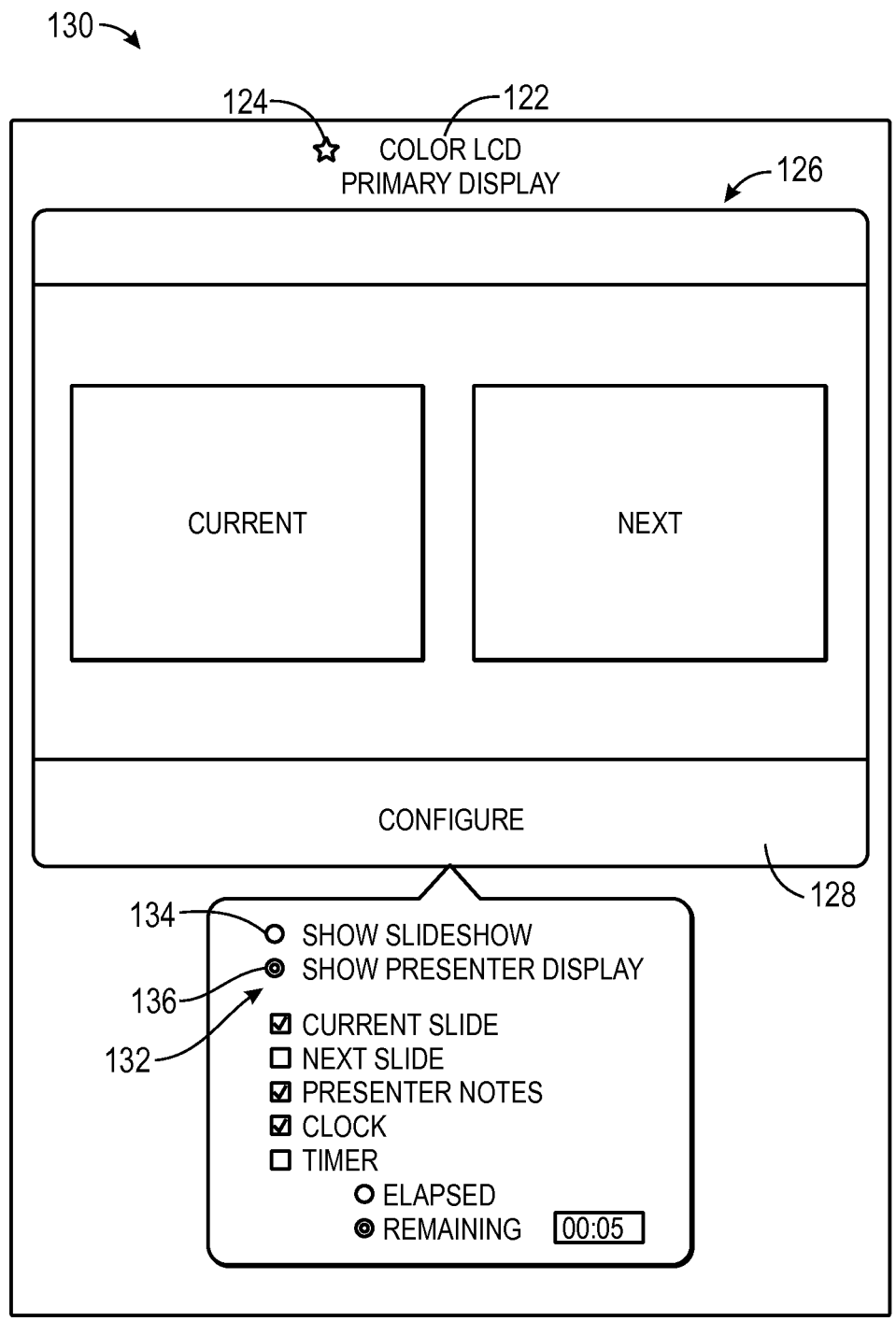

Selecting the configuration button 128 may cause the display of a screen segment 130 shown in FIG. 11. Specifically, when the presenter selects the configuration button 128, a configuration pane 132 may allow the presenter to determine whether that particular display 12 will be a main presentation (MP) display (e.g., via a radio button 134) or will be a presenter display (PD) (e.g., via a radio button 136). When the presenter has decided to configure the display 12 to be a presenter display (PD), as illustrated in FIG. 11, the presenter also may select what information to show on that presenter display (PD), such as the current slide, the next slide, presenter notes, a clock, and/or a timer.

The information described in this disclosure as useful to aid the presenter in carrying out a successful and effective presentation is provided by way of example and is not intended to be exhaustive. Indeed, any suitable information that may assist the presenter, other than the fullscreen view of the presentation as displayed on a main presentation (MP) display, may be used on one or more of the presenter displays (PDs).

When the electronic device 10 running the presentation program is connected to more than one electronic display 12, the displays 12 not showing the presentation may provide such information to aid the presenter to great effect. In some embodiments, all of the electronic displays 12 that do not display the presentation as the main presentation (MP) display may represent primary presenter displays (PD1s) that include a control tool bar 62. In other embodiments, however, of the remaining electronic displays 12 that do not display the presentation as a main presentation (MP) display, only one or more may represent the primary presenter display (PD1) and other remaining of the electronic displays 12 may represent secondary presenter displays (e.g., PD2, PD3, PD4, and so forth).

Figure 12:
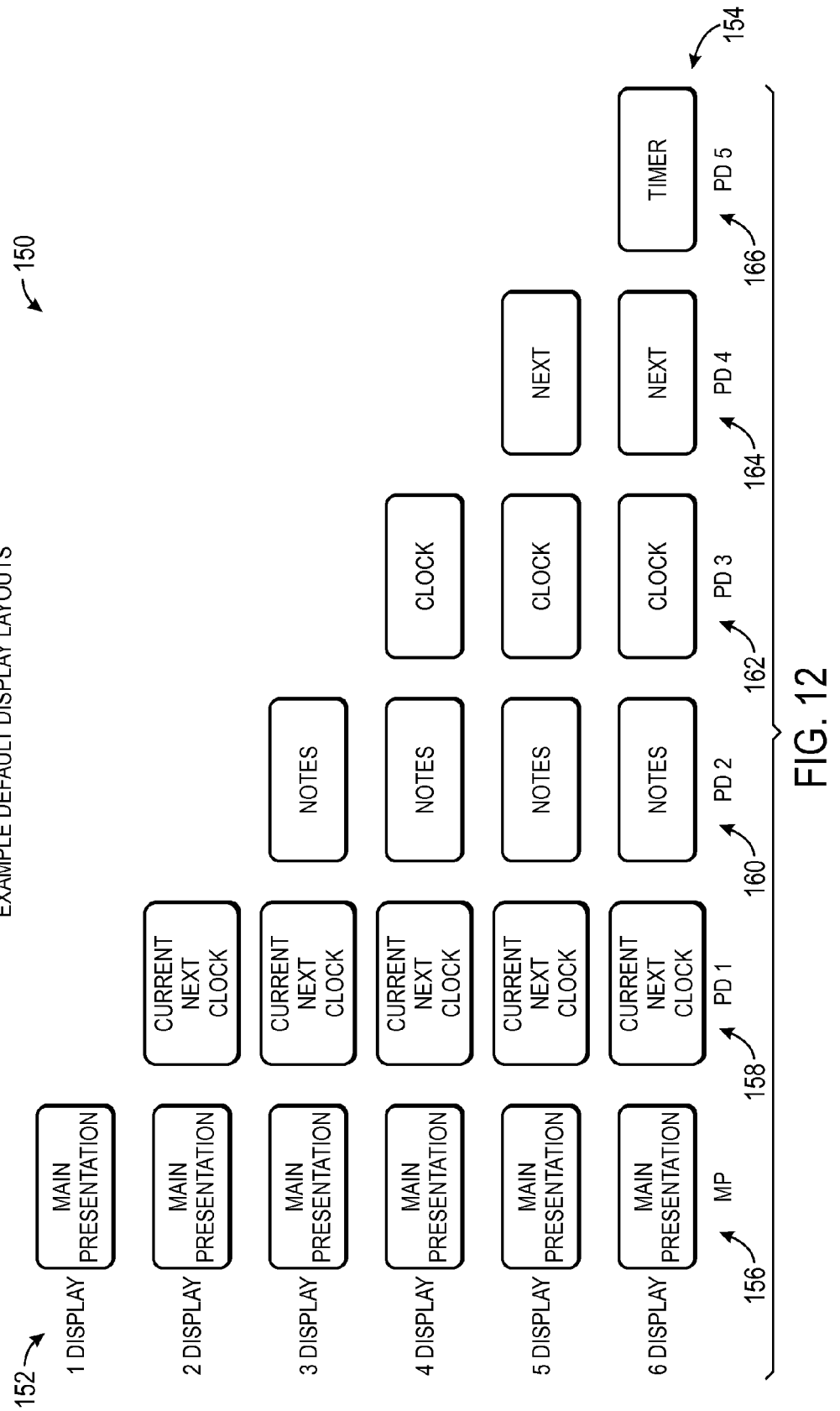
FIG. 12 is a chart illustrating one example of a default set of multi-display presenter display layouts, in accordance with an embodiment.

When multiple electronic displays 12 are connected to the electronic device 10, the electronic device 10 may apply a default display layout depending on the number of electronic displays 12 that are connected. A chart 150 shown in FIG. 12 illustrates one example default display layout that may be used. An ordinate 152 of the chart 150 represents the number of displays 12 that are connected to the electronic device, and an abscissa 154 represents the order in which the various electronic displays 12 are assigned. For instance, according to the example chart 150, a first display 156 of the electronic displays 12 may always represent the main presentation (MP) display regardless of the number of displays 12 connected to the electronic device 10. A second display 158, when there are two or more displays 12, may be chosen to represent a primary presenter display (PD 1). In the example of FIG. 12, subsequent electronic displays 12 may be secondary presenter displays (PD2, PD3, PD4, and so forth) that display certain respective information by default. For example, a third display 160 may be a second presenter display (PD2), a fourth display 162 may be a third presenter display (PD3), a fifth display 164 may be a fourth presenter display (PD4), and a sixth display 166 may be a fifth presenter display (PD5). In the example of FIG. 12, these subsequent presenter displays 160, 162, 164, and 166 display, by default, notes, clock, next slide, and a timer, respectively.

It should be understood that the default information shown in the various presenter displays (PDs) 158, 160, 162, 164, and 166 is provided by way of example and is not meant to be exhaustive. Moreover, the particular information provided by way of default may also be influenced by the particular features and/or characteristics of the individual electronic displays 12 to which they are assigned. For example, when the displays 158, 160, 162, 164, and/or 166 are larger than a threshold size or resolution, additional information may be included on each by default that is not included otherwise.

When it comes time for a presenter to perform a slide presentation before an audience, the presenter may not want to spend time configuring the display layout for the presentation. Accordingly, the electronic device 10 running the presentation program 34 may automatically configure the presentation display layout when the electronic device 10 enters a presentation mode, is connected to another electronic display 12 (e.g., while running the slide presentation program), and/or is disconnected from a connected electronic display 12 (e.g., while running the slide presentation program). In this way, a presenter may seamlessly and professionally perform presentations—even in unfamiliar locations or with late notice—without first configuring the display configuration while the audience watches and waits.

Figure 13:
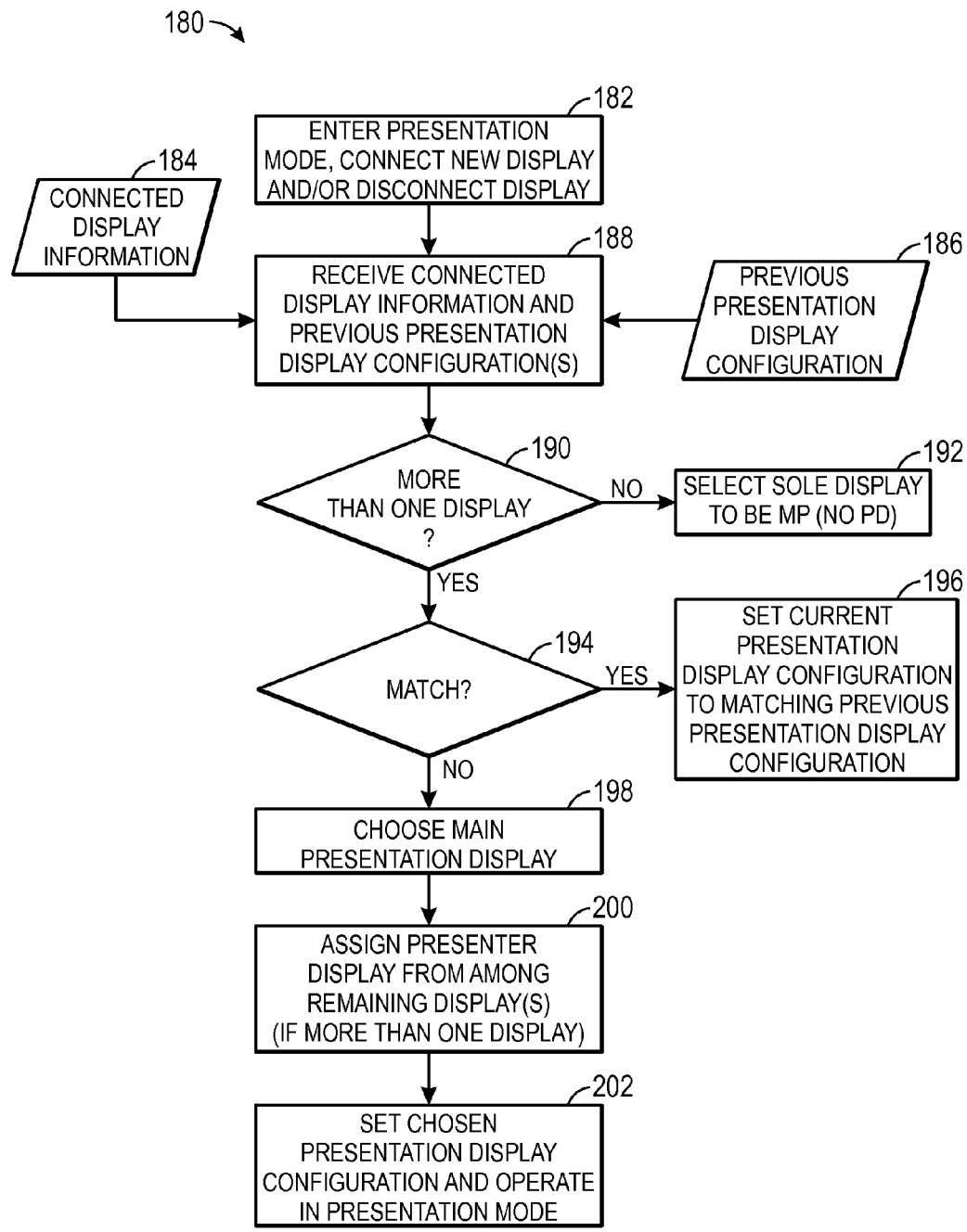
FIG. 13 is a flowchart for automatically configuring a presentation display layout based at least partly on connected display information relating to a set of currently connected electronic displays, in accordance with an embodiment.

A flowchart 180 of FIG. 13 provides one example of a process for automatically configuring the connected displays 12 for displaying a presentation. The flowchart 180 may begin when the presenter causes the electronic device 10 to enter a presentation mode, connect to another display 12, and/or disconnect from a connected electronic display 12 (block 182). The electronic device 10 may receive and consider connected display information 184 that describes the currently connected electronic displays 12 and/or indications of previous presentation display layout(s) 186 (block 188). Using at least the connected display information 184, the electronic device 10 may automatically configure the presentation display layout by applying a previously determined presentation display layout from one of the previous presentation display layout(s) 186 or by prioritizing the connected displays 12 by those likely to be preferred by the presenter to be the main presentation (MP) display or a presenter display (PD). Before continuing, as used herein, the connected display information 184 may be any suitable information that describes the set of the various electronic displays 12 currently connected to the electronic device 10. This information may include, for example, information provided by the electronic displays 12 themselves (directly or via an operating system (OS) of the electronic device 10), or system-level services from the operating system (OS).

Display Information Provided by the Electronic Displays.

The electronic displays 12 themselves may provide certain information that may be included in the connected display information 184 through data such Extended Display Identification Data (EDID) and/or DisplayID, which are standards of the Video Electronics Standards Associate (VESA). The information provided by such data may include a unique identifier, an indication of the manufacturer, the date of manufacture, a manufacturer product code, operational parameters and characteristics (e.g., screen size, resolution, and so forth), color capabilities, and/or timing information, and so forth. The electronic device 10 may use any suitable fields of such data as the EDID or DisplayID that may be relevant to the operation or identification of each electronic display 12 to carry out the techniques of this disclosure.

System-Level Services from the Operating System (OS).

The connected display information 184 may also include information about the connected electronic displays 12 determined and/or provided by the operating system (OS) of the electronic device 10. Such information may include, for example, an indication of whether an electronic display 12 is internal or external to the electronic device 10, a determination of the type of the electronic display 12 (e.g., projector, television, or so forth), a screen size of the electronic display 12, and/or the screen resolution of the electronic display 12 (e.g., the maximum screen resolution or the screen resolution currently used by the operating system (OS) when sending image data to that electronic display 12).

In summary, the connected display information 184 provides information that the electronic device 10 may use to determine, automatically, a likely display layout that the presenter will prefer given the currently connected set of electronic displays 12. By way of example, and as will be discussed further below, a presenter who connects a notebook computer to a number of electronic displays 12, one of which is a very large projector, is not likely to want the main presentation (MP) display to appear on the internal display 12 of the notebook computer 10C. Rather, the presenter is likely to prefer that the main presentation (MP) display is the projector 54. Thus, the electronic device 10 may use the connected display information 184 to automatically select a default display layout in which the projector 54 is the main presentation (MP) display and the internal display 12 is the primary presenter display (PD1) based at least partly on the connected display information 184. The previous presentation display layout(s) 186 may represent previous configurations (e.g., presentation display layouts) that have been stored by the electronic device 10 when the electronic device 10 was previously connected to a previous set of electronic displays 12.

Still considering the flowchart 180 of FIG. 13, the electronic device 10 may initially ascertain whether the connected display information 184 indicates that the electronic device 10 is connected to more than one display 12 (decision block 190). If not, the electronic device 10 may select the sole electronic display 12 to be the main presentation (MP) display and may not select that sole electronic display 12 to be a presenter display (PD). This may be the case even if the process of the flowchart 180 began at block 182 with the disconnection of an electronic display 12. For instance, the presenter's notebook computer 10C may be connected to a projector 54 operating as the main presentation (MP) display and the internal display 12 of the notebook computer 10C may be serving as a primary presenter display (PD1). When the presenter disconnects the projector 54, leaving only the single internal display 12 connected to the notebook computer 10C, the internal display 12 may switch from being the primary presenter display (PD1) to being the main presentation (MP) display.

On the other hand, when the connected display information 184 indicates that there are multiple connected electronic displays 12 (decision block 190), the electronic device 10 may next consider whether the connected display information 184 matches any previous presentation display layout(s) 186 (decision block 194). If there is a match or substantial match, the electronic device 10 may assign roles to the various electronic displays 12 according to the matching previous presentation display layout 186.

As used herein, the term "match" may refer to an exact match or a substantial match. In an exact match, the connected display information 184 indicates that the electronic device 10 has a previous presentation display layout 186 has been determined for the exact same electronic displays 12 (e.g., as indicated by a unique identifier and/or serial number associated with each electronic display 12). This may be the case when a presenter repeatedly performs slide presentations at different times in the same meeting room. For instance, a presenter may regularly perform slide presentations to a team of colleagues on a weekly or monthly basis in a particular meeting room. Under these circumstances, a tremendous amount of time and effort may be saved on the part of the presenter to avoid reconfiguring the presentation display layout every time the presenter performs a slide presentation in that meeting room.

In contrast to an exact match, a "substantial match" may occur when the connected display information 184 does not indicate that the exact same electronic displays 12 have been previously connected to by the electronic device 10, but rather that the characteristics of the currently connected set of electronic displays 12 are very similar to those of a previously connected set of electronic displays 12. For example, the presenter may have previously configured a presentation display layout for a projector 54 and a television 52 connected to a notebook computer 10C in a first room. This may be stored as a previous presentation display layout 186 in association with that set of connected electronic displays 12. When the presenter performs a presentation in a different, but similarly outfitted room with a different projector 54 and television 52, the electronic device 10 may determine that there is a substantial match, even though the electronic device 10 has never connected to these exact electronic displays 12. That is, a substantial match indicates that the presenter is likely to prefer that a previous configuration associated with a first set of electronic displays 12 be applied to an unfamiliar, but similar, second set of electronic displays 12.

The electronic device 10 may ascertain that the connected display information 184 substantially matches a previous presentation display layout 186 by comparing, for example, whether a previous presentation display layout 186 is associated with a previously connected set of electronic displays 12 having some threshold amount of similarity. For instance, when the electronic device 10 connects to a new set of electronic displays 12 that differ from a previous set of electronic displays 12 by unique identification numbers and/or serial numbers, but for which most other characteristics of DisplayID or EDID data is the same, the electronic device 10 may ascertain a substantial match. In another example, the electronic device 10 may ascertain a substantial match when all but a threshold number of fields of the DisplayID or EDID data from the electronic displays 12 are the same. In another example, the electronic device 10 may ascertain a substantial match when the connected display information 184 indicates that the particular types of electronic displays 12 currently connected to the electronic device 10 (e.g., as indicated by the operating system-level services) are the same as a previously connected set of electronic displays 12. By way of example, the electronic device 10 may have a previous presentation display layout 186 associated with connecting to a set of electronic displays 12 including an internal display 12, a projector 54, and a television 52. When the electronic device 10 is later connected to a different set of electronic displays 12 identified as the internal display 12, a different projector 54, and a different television 52, the electronic device 10 may ascertain a substantial match and may apply the previous presentation display layout 186.

Even if there is no exact or substantial match (decision block 194), the electronic device 10 may still automatically determine an initial presentation display layout based on the connected display information 184 without an explicit user assignment of the electronic displays 12 to particular roles in the presentation program. The electronic device 10 may consider the connected display information 184 to choose a main presentation (MP) display (block 198) and assign presenter displays (PDs) from among any remaining electronic displays 12, provided that the electronic device 10 is connected to more than one electronic display 12 (block 200). The electronic device 10 may set the presentation display layout that has been automatically chosen and begin to operate in the presentation (e.g., play) mode (block 202).

Figure 14:
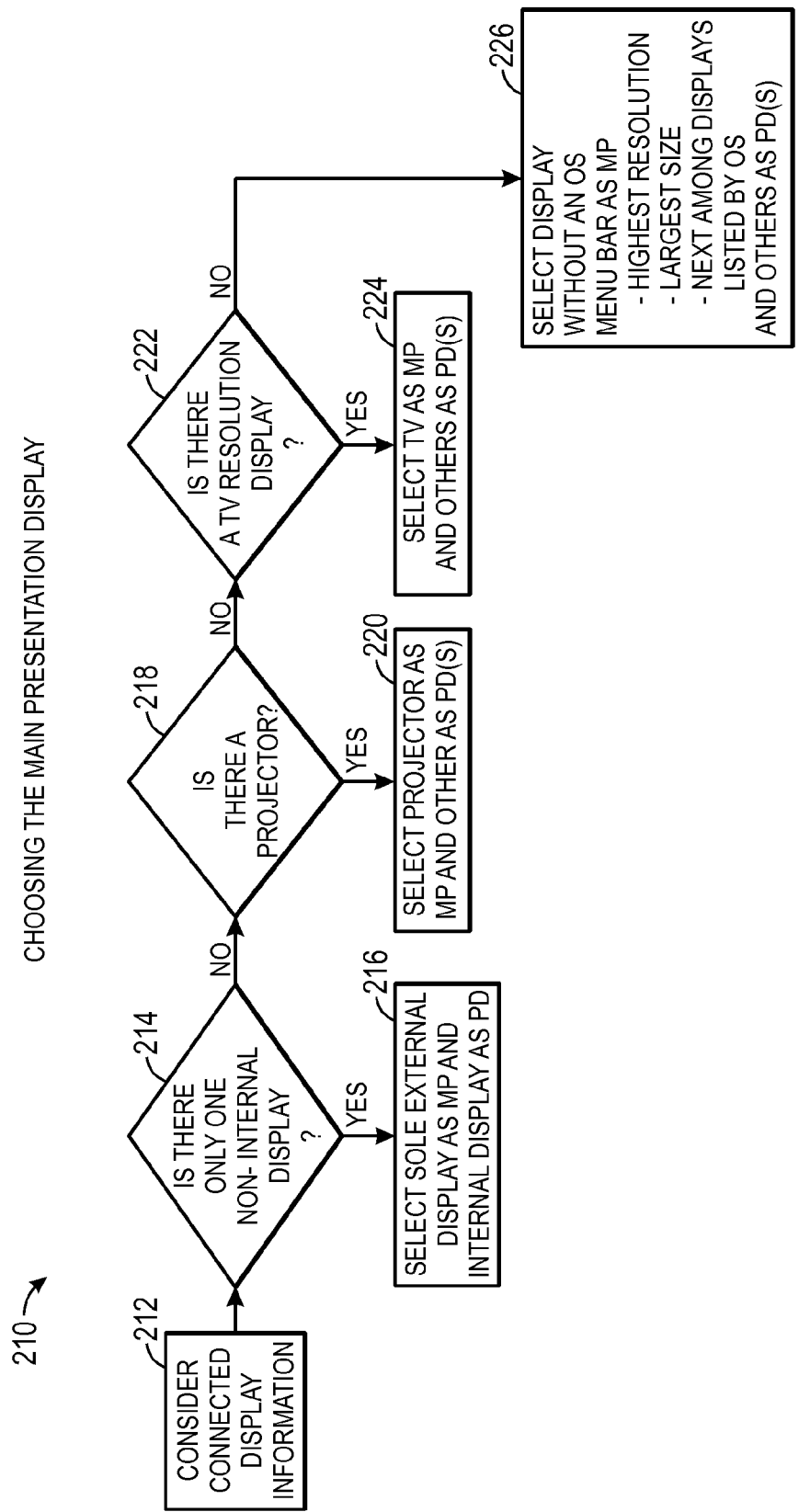
FIG. 14 is a flowchart of a method for choosing which connected display to be a main presentation (MP) display, in accordance with an embodiment.

The electronic device 10 may automatically chose the main presentation (MP) display from among the connected electronic displays 12 using any suitable technique that prioritizes the displays 12 from expected user presenter preferences. The priority based on expected user preferences may be determined in any suitable manner (e.g., through experimentation, statistical analysis of user feedback, and so forth). An example of flowchart 210 of FIG. 14 provides one example of an automatic prioritized selection of the main presentation (MP) display as indicated at block 198 of FIG. 13. As shown in FIG. 14, the electronic device 10 may consider the connected display information 184 to ascertain properties of the currently connected electronic displays 12 (block 212). If the connected display information 184 indicates that there is only one non-internal electronic display 12 (decision block 214) the electronic device 10 may select the sole external display 12 to be the main presentation (MP) display and the remaining internal display to be a presenter display (PD) (block 216).

In some embodiments, the internal display 12 may be chosen to be the main presentation (MP) display instead of the external display 12 at block 216 when the external display 12 includes an operating system (OS) menu bar. This placement of the OS menu bar may indicate that the external display 12 is the display that the presenter uses for primary control over the electronic device 10. That is, when the external display 12 contains the OS menu bar, then, the presenter may prefer to continue using the external display 12 to control the external device 10 as the primary presenter display (PD1). Alternatively, if the internal display 12 does not have an OS menu bar, the internal display 12 may be treated as an external display for the purposes of the process 210 of FIG. 14. Moreover, in some embodiments, the presenter may provide a contemporaneous indication of preference for a different display. For example, the presenter may press the "x" key to cause the next electronic display 12 in the priority of electronic displays 12 as may be determined, for example, by the process 210 of FIG. 14.

If there are multiple external displays 12 connected to the electronic device 10, the electronic device 10 may select the main presentation (MP) display by prioritizing from among the multiple external displays 12. For instance, if one of the connected electronic displays 12 is indicated to be a projector 54 (decision block 218), the projector 54 may be selected as the main presentation (MP) display and all other electronic displays may be defined to be presenter displays (PDs) (block 220). When there are multiple projectors 54 connected to the electronic device 10, the electronic device 10 may select the main presentation (MP) display by prioritizing the multiple projectors 54. For instance, the electronic device 10 select from among the multiple projectors 54 that which has the highest resolution, largest size, or that is next among the electronic displays 12 categorized by the operating system (OS). Additionally or alternatively, if one of the projectors 54 includes an operating system (OS) menu bar, a different one of the projectors 54 that does not include an OS menu bar may be selected as the main presentation (MP) display. In some embodiments, multiple projectors 54 having substantially the same characteristics may all be selected to be main presentation (MP) displays because this may suggest an auditorium or meeting room with multiple audience focal points.

If there is not a projector (decision block 218), the electronic device 10 may consider whether any of the multiple external electronic displays 12 is identified as a television 52 (e.g., is an electronic display 12 that has a television resolution or is explicitly identified by the operating system (OS) as a television 52) (decision block 222). If so, the electronic device may select the television 52 to be the main presentation (MP) display and all others as presenter displays (PDs) (block 224). As in the case of multiple projectors 54, when there are multiple televisions 52, the electronic device 10 may select the main presentation (MP) display by prioritizing the multiple televisions. The electronic device 10 select from among the multiple televisions 52 that which has the highest resolution, largest size, or that is next among the electronic displays 12 categorized by the operating system (OS). Additionally or alternatively, if one of the televisions 52 includes an operating system (OS) menu bar, a different one of the televisions 52 that does not include an OS menu bar may be selected as the main presentation (MP) display. In some embodiments, multiple televisions 52 having substantially the same characteristics may all be selected to be main presentation (MP) displays because this may suggest an auditorium or meeting room with multiple audience focal points.

When there are multiple electronic displays 12 and there is neither a projector (decision block 218) nor a television (decision block 222) among those multiple external displays 12, the electronic device 10 may prioritize them based on other characteristics. For instance, the electronic device 10 may select one of the multiple electronic displays 12 that does not include an OS menu bar that has the highest resolution, largest size, or that is next among the electronic displays 12 categorized by the operating system (OS) (block 226). The other electronic displays 12 not selected to be the main presentation (MP) display may be categorized as presenter displays (PDs).

Figure 15:
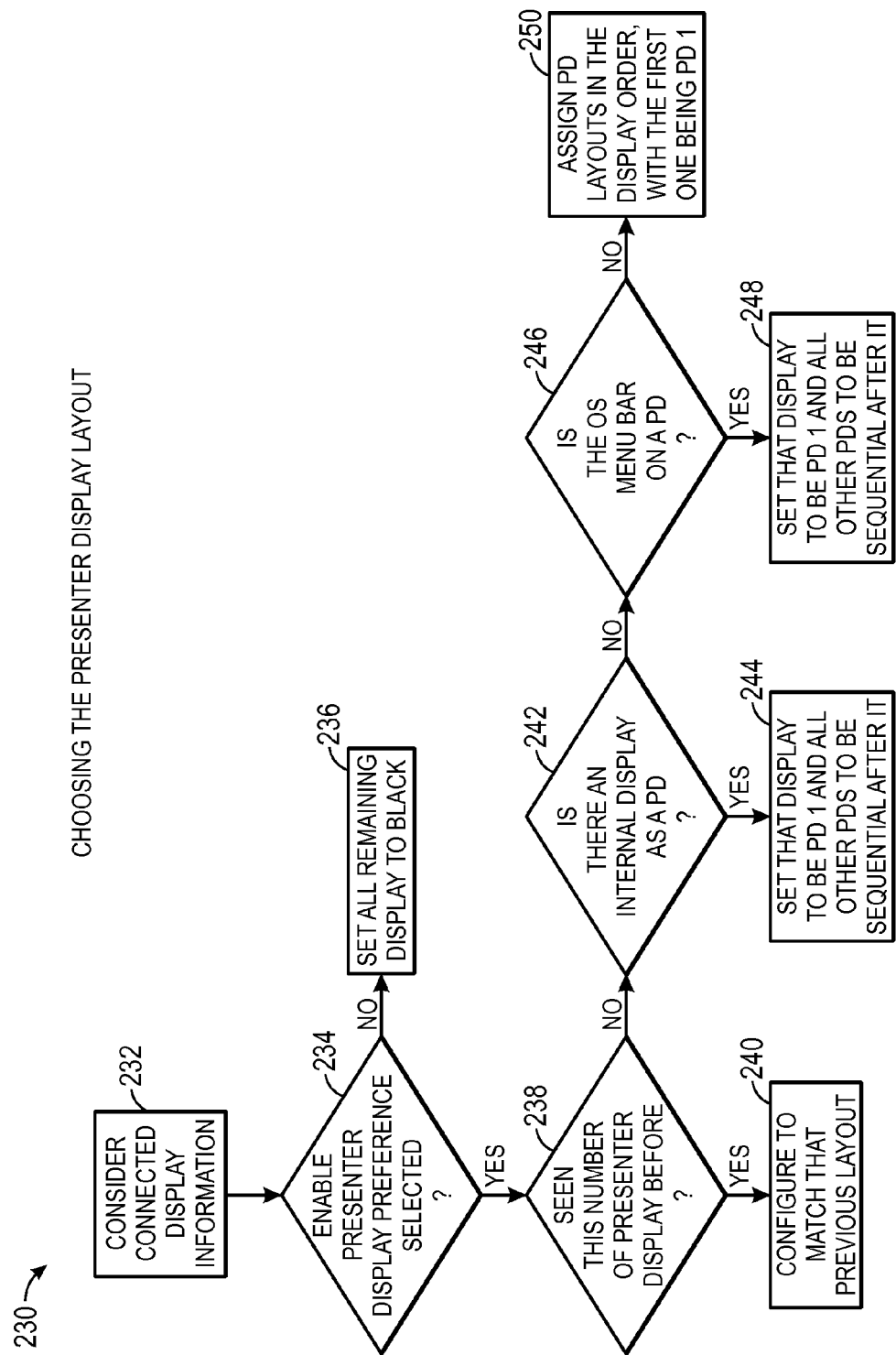
FIG. 15 is a flowchart of a method for choosing a presenter display (PD) layout among the remaining connected electronic display(s), in accordance with an embodiment.

Having assigned the main presentation (MP) display and identified which of the electronic displays 12 will be presenter displays (PDs), the electronic device 10 may assign the particular presenter displays (PDs) to be a primary presenter display (PD1) and/or secondary presenter displays (PD2, PD3, PD4, and so forth), as indicated at block 200 of FIG. 13. A flowchart 230 of FIG. 15 provides one example from a method for automatically selecting the display layout of the presenter displays (PDs) based on the connected display information 184. The electronic device 10 may consider the connected display information 184 relating to particular characteristics of the various connected electronic displays 12 (block 232). If a presenter display preference is indicated as not selected (decision block 234), all of the electronic displays 12 that have not been identified as the main presentation (MP) display may be set to particular image (e.g., a neutral color such as black) (block 236). Otherwise, when the presenter display preference has been selected (decision block 234), the electronic device 10 may consider whether this number of presenter displays has been previously connected to the electronic device 10 (decision block 238). If so, this may indicate that the presenter has particular preferences for the various presenter information to be laid out on the various electronic displays 12, even if the exact same electronic displays 12 have not been connected to in the past. Thus, the electronic device 10 may recall the previous preferences of the presenter for the individual presenter displays PD1, PD2, PD3, and so forth instead of applying defaults, such as those described above in the chart 150 of FIG. 12. If the electronic device 10 has not been connected to this number of presenter displays (decision block 238), the electronic device 10 may apply the default presenter display characteristics, as described, for example, by the chart 150 of FIG. 12.

In either case, the electronic device 10 may assign the remaining electronic displays 12 to be particular presenter displays (e.g., PD1, PD2, PD3, and so forth) by prioritizing the electronic displays 12 based on the characteristics indicated by the connected display information 184. For instance, if there is an internal display 12 that has been set as a presenter display (PD) rather than the main presentation (MP) display (decision block 242), that internal display 12 may be set to be the primary presenter display (PD1) (block 244). All of the other presenter displays (PDs) may be prioritized (e.g., based on the presence or absence of a OS menu bar, the screen size, screen resolution, and/or being the next among displays 12 listed by the operating system (OS)).

If there is not an internal display 12 that is set to be a presenter display (PD) decision block 242, the electronic device 10 may consider whether an operating system (OS) menu bar is located on a presenter display (PD) (decision block 246). If so, that electronic display 12 may be set to be the primary presenter display (PD1) and all other remaining electronic displays 12 assigned to be presenter displays (PDs) may be assigned sequentially after that one in the manner discussed above. Otherwise, if there is neither an internal display 12 that is set as a presenter display (PD) (decision block 242) nor an OS menu bar on a presenter display (decision block 246), the presenter displays (PDs) may be assigned in order according to other priorities (e.g., the screen size, screen resolution, and/or being the next among displays 12 listed by the OS) (block 250).

By automatically assigning the presentation display layout when entering the presentation mode or when an electronic display 12 is connected or disconnected, a significant burden on the presenter may be avoided. A presenter may configure a particular set of electronic displays 12 in a particular room or auditorium in advance, and when the presenter reconnects the electronic displays 12, the presenter's electronic device 10 may automatically recall the saved presentation display layout without requiring additional configuration on the presenter's part while the audience watches and waits. Likewise, by automatically prioritizing electronic displays 12 even that have never been previously connected to the presenter's electronic device 10, the electronic device 10 may save the user from frustration and embarrassment when performing a slide presentation in an unfamiliar environment. The presenter may simply connect his or her electronic device 10 to a new set of electronic displays 12. The electronic device 10 may automatically prioritize the electronic displays 12 as discussed above, allowing the presenter to focus on delivering the presentation.

In certain embodiments, the presentation program 34 may have other modes than the edit mode and the presentation mode. For example, the presentation program 34 may also include a rehearse mode in which only the primary presenter display (PD1) is active and all other displays 12 are set to a particular image (e.g., a neutral color such as black). As illustrated by a flowchart 260 of FIG. 16, the electronic device 10, upon entering the rehearse mode (block 262), may chose a main presentation (MP) display and set it to a particular image (e.g., a neutral color such as black) (block 264). The main presentation (MP) display may be selected in the same manner as discussed above with reference to FIG. 14. Likewise the flowchart 260 may involve determining the primary presenter display (PD1) in substantially the same manner as in the flowchart 230 of FIG. 15. That is, if there is an internal display not selected as the main presentation (MP) display (decision block 266), that display may be set to be the primary presenter display (PD1) and all other PDs may be set to show a neutral image such as black (block 268). Otherwise, if there is a menu bar on one of the electronic displays not selected as the main presentation (MP) display (decision block 270), that display may be set to be the primary presenter display (PD1) and all other electronic displays 12 may be set to a neutral image such as black (block 272). If none of the non-main-presentation (MP) displays are internal displays (as in decision block 266) or have an OS menu bar (as in decision block 270), the primary presenter display (PD1) may be determined according to any suitable priority (e.g., the screen size, screen resolution, and/or being the next among displays 12 listed by the operating system (OS)) (block 274). Having ascertained a primary presenter display (PD1) automatically, the presenter may rehearse the slide presentation without revealing the presentation to any audience that may be present and without spending precious time manually configuring the display layout.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method comprising:
   receiving, into one or more processors of an electronic device, connected display information that describes electronic displays currently connected to the electronic device;
   based on the connected display information indicating that multiple electronic displays are currently connected to the electronic device, using the one or more processors to automatically choose without explicit user assignment:
      a main presentation display to display a slide presentation from among the multiple electronic displays;
      one or more presenter displays to display information other than only the slide presentation from among the one or more multiple electronic displays not chosen to be the main presentation display; and
      a primary presenter display that includes a graphical presentation control interface lacking on all other of the plurality of presenter displays;
   while running a slide presentation program on the electronic device currently connected to the multiple electronic displays, receiving an indication in the electronic device that the electronic device has been connected to an additional electronic display; and
   based at least in part on the connected display information, assigning the additional electronic display as the main presentation display and re-assigning the multiple electronic displays to be either the one or more presenter displays or the primary presenter display.

2. The method of claim 1, wherein the main presentation display and the one or more presenter displays are chosen based at least in part on an indication by the connected display information that one of the multiple electronic displays is an internal display, an external display, a television, a projector, or a primary display of an operating system running on the processor, or any combination thereof.

3. The method of claim 1, wherein the main presentation display is assigned such that:

if, based on the connected display information, only one external display is indicated as connected to the electronic device, then the only one external display is assigned as the main presentation display;
   if, based on the connected display information, more than one external display is indicated as connected to the electronic device and one or more of the external displays is a projector, then the one or more projectors is assigned as the main presentation display;
   if, based on the connected display information, more than one external display is indicated as connected to the electronic device, none of the external displays is a projector, and one or more of the external displays is a television, then the one or more televisions is assigned as the main presentation display; and
   if, based on the connected display information, more than one external display is indicated as connected to the electronic device and none of the external displays is a projector or television, then a one or more of the external displays is assigned as the main presentation display based on one or more of display resolution, display size, or operating system prioritization as determined from the connected display information.

4. The method of claim 1, wherein the method is performed upon entering a presentation mode of a slide presentation program.

5. The method of claim 1, wherein the method is performed upon connecting another electronic display while running a slide presentation program.

6. The method of claim 1, wherein the method is performed upon disconnecting one of the multiple electronic displays while running a slide presentation program.

7. The method of claim 6, comprising, when disconnecting the one of the multiple electronic displays results in only one electronic display being connected to the electronic device, using the processor to automatically choose, without explicit user selection, the only one electronic display as the main presentation display in response to the only one electronic display was previously chosen as one of the one or more presenter displays and when the only one electronic display was previously chosen as the main presentation display.

8. An electronic device for performing a slide presentation comprising:
   an internal electronic display; and
   at least one processor configured to run a slide presentation program to perform the slide presentation, wherein, when one or more external electronic displays are connected to the electronic device while the slide presentation is running, the processor is configured to:
      obtain connected display information describing the internal electronic display and the one or more external electronic displays, wherein the connected display information comprises:
         one or more DisplayID or EDID fields for each respective electronic display; and
         one or more display descriptions determined by an operating system running on the processor, wherein the one or more display descriptions comprises an indication of whether the described display is the internal display or one of the one or more external displays;
      assign at least one of a group of the internal electronic display and the one or more external electronic displays, based at least in part on the connected display information, to be a main presentation display that displays the slide presentation in full screen, and a remainder of the group of the internal electronic display and the one or more external electronic displays to be a plurality of presenter displays that display information other than a full-screen view of the slide presentation, wherein the plurality of presenter displays comprises a primary presenter display that includes a graphical presentation control interface lacking on all other of the plurality of presenter displays; and in response to an additional electronic display being connected to the electronic device while the slide presentation is running and after the slide presentation is started, automatically assign, based at least in part on the connected display information, the additional electronic display to be the main presentation display and re-assign the group of the internal electronic display and the one or more external electronic displays, based at least in part on the connected display information, to be the plurality of presenter displays, wherein the plurality of presenter displays comprises the primary presenter display.

9. The electronic device of claim 8, wherein the processor is configured to assign each of the group of the internal electronic display and the one or more external electronic displays by:

comparison of the connected display information to a previous presentation display configuration that is associated with a previous set of electronic displays that was previously connected to the electronic device, wherein the previous presentation display configuration describes an assignment of each of the previous set of electronic displays to a respective role in the slide presentation program; and when the connected display information matches the previous set of electronic displays, assign each of the electronic displays currently connected to the electronic device the respective role in the slide presentation program prescribed by the previous presentation display configuration when there is a match.

10. The electronic device of claim 8, wherein the processor is configured to assign by default one of the one or more external electronic displays to be the main presentation display and to assign the internal electronic display to be one of the plurality of presenter displays.

11. The electronic device of claim 10, wherein the processor is configured to assign the internal electronic display to be the primary presenter display.

12. The electronic device of claim 8, wherein the one or more DisplayID or EDID fields for each respective electronic display comprise one or more identification fields that uniquely identify that respective electronic display.

13. The electronic device of claim 8, wherein the one or more DisplayID or EDID fields for each respective electronic display comprise information relating to resolution, size, or type, or any combination thereof, of that respective electronic display.

14. The electronic device of claim 8, wherein the one or more display descriptions determined by an operating system running on the processor comprise information relating to resolution, size, and type, or any combination thereof, of each respective electronic display.

15. One or more tangible, non-transitory machine-readable media comprising instructions to:

obtain connected display information providing characteristics of a first set of electronic displays currently connected to an electronic device;

obtain a previous presentation display configuration associated with a second set of electronic displays previously connected to the electronic device, wherein the previous presentation display configuration describes an assignment of each of the electronic displays of the second set of electronic displays to a respective role in a slide presentation program;

determine whether the first set of electronic displays matches the second set of electronic displays;

when the first set of electronic displays matches the second set of electronic displays, assign each of the electronic displays currently connected to the electronic device a respective role in the slide presentation program according to the previous presentation display configuration; and when the first set of electronic displays does not match the second set of electronic displays, assign each of the electronic displays currently connected to the electronic device a respective role in the slide presentation program based on the connected display information so as to correspond to the previous presentation display configuration.

16. The machine-readable media of claim 15, wherein the first set of electronic displays is determined to exactly match the second set of electronic displays when all of the connected display information associated with the first set of electronic displays matches previous connected display information associated with the second set of electronic displays.

17. The machine-readable media of claim 15, wherein the first set of electronic displays is determined to exactly match the second set of electronic displays when each electronic display of the first set of electronic displays shares a respective common unique identifier.

18. The machine-readable media of claim 17, wherein the unique identifiers are from a field from DisplayID or EDID data deriving from each electronic display.

19. The machine-readable media of claim 17, wherein the unique identifiers are values that attempt to uniquely identify the electronic displays based at least in part on the characteristics of the electronic displays indicated by the connected display information other than DisplayID or EDID data.

20. The machine-readable media of claim 15, wherein the first set of electronic displays is determined to substantially match the second set of electronic displays when more than a threshold amount of the connected display information associated with the first set of electronic displays exactly matches previous connected display information associated with the second set of electronic displays.

21. The machine-readable media of claim 15, wherein the first set of electronic displays is determined to substantially match the second set of electronic displays when more than a threshold number of EDID or DisplayID fields associated with the first set of electronic displays exactly matches respective EDID or DisplayID fields associated with the second set of electronic displays.

22. A method comprising:

while running a slide presentation program on an electronic device connected to a first electronic display, receiving an indication in the electronic device that the electronic device has been connected to a second electronic display; and automatically, in the electronic device, assigning the second electronic display that is connected during the running of the slide presentation program to be a main presentation display that displays a slide presentation in full screen and re-assigning the first electronic display to be a presenter display that displays information to aid a presenter other than a full-screen representation of the slide presentation based at least in part on characteristics of the first and second electronic displays, wherein the information to aid the presenter comprises a graphical presentation control interface.

23. The method of claim 22, wherein the characteristics of the first and second electronic displays include indications that the second electronic display is a projector and that the first electronic display is not a projector, and wherein the second electronic display is assigned to be the main presentation display and the first electronic device is assigned to be the presenter display.

24. The method of claim 22, wherein the characteristics of the first and second electronic displays include indications that the second electronic display does not include an operating system menu bar and that the first electronic display does include the operating system menu bar, and wherein the second electronic display is assigned to be the main presentation display and the first electronic device is assigned to be the presenter display.

25. One or more tangible, non-transitory machine-readable media comprising instructions to:
   receive, via an electronic device, a user request to enter a rehearse mode in a slide presentation program running on the electronic device;
   while in the rehearse mode, assign, via the electronic device, one of a plurality of electronic displays currently connected to the electronic device to be a primary presenter display, wherein the primary presenter display comprises a graphical presentation control interface; and
   while in the rehearse mode, cause, via the electronic device, all of the currently connected displays except the primary presenter display to display a particular image while information relevant to aid a presenter of a slide presentation is displayed on the primary presenter display such that information in the slide presentation program is not displayed on the currently connected displays except for the primary presenter display.

26. The machine-readable media of claim 25, wherein the particular image is a black screen.

27. The machine-readable media of claim 25, wherein the instructions to assign the one of the plurality of electronic displays to be the primary presenter display comprise instructions to first assign a different one of the plurality of electronic displays to be a main presentation display that would, in a presentation mode, display a full screen view of the slide presentation, before selecting from among the remaining ones of the plurality of electronic displays to be the primary presenter display.

* * * * *